United States Patent [19]
Urchuk et al.

[11] Patent Number: 5,848,117
[45] Date of Patent: Dec. 8, 1998

[54] APPARATUS AND METHOD FOR COMPUTED TOMOGRAPHY SCANNING USING HALFSCAN RECONSTRUCTION WITH ASYMMETRIC DETECTOR SYSTEM

[75] Inventors: Steven N. Urchuk, Melrose; Christopher C. Ruth, Danvers; Carl R. Crawford, Brookline, all of Mass.

[73] Assignee: Analogic Corporation, Peabody, Mass.

[21] Appl. No.: 904,516

[22] Filed: Aug. 1, 1997

Related U.S. Application Data

[63] Continuation-in-part of Ser. No. 829,062, Mar. 31, 1997, which is a continuation of Ser. No. 759,368, Mar. 27, 1996, abandoned.

[51] Int. Cl.⁶ ........................................ A61B 6/03
[52] U.S. Cl. .................. 378/19; 378/15; 378/901
[58] Field of Search ................... 378/15, 19, 901

[56] References Cited

U.S. PATENT DOCUMENTS 4,637,040  1/1987  Sohval et al. ............................. 378/9

OTHER PUBLICATIONS

Dennis L. Parker, "Short scan convolution reconstruction for fanbeam CT", Med. Phys. 9(2), Mar./Apr. 1982, pp. 254–257.

Carl R. Crawford et al, "Computed tomography scanning with simultaneous patient translation" Med. Phys. 17(6), Nov./Dec. 1990, pp. 967–982.

Harish P. Hiriyannaiah, "X–ray Computed Tomography for Medical Imaging", Mar. 1997, pp. 42–59.

*Primary Examiner*—David P. Porta
*Assistant Examiner*—David Vernon Bruce
*Attorney, Agent, or Firm*—Lappin & Kusmer LLP

[57] ABSTRACT

A method and apparatus for halfscan reconstruction in a CT scanning system using an asymmetric detector system are described. In halfscan asymmetric (HSA) reconstruction, a halfscan reconstruction approach is used for data acquired by the symmetric portion of the array, and a fullscan reconstruction approach is used to reconstruct data acquired by the asymmetric portion of the array. When scanning oversized subjects which extend beyond the symmetric field of view of the array, a halfscan reconstruction approach is used which applies a zero weighting to data acquired by the asymmetric portion of the array and ramps data acquired by the asymmetric portion to zero.

32 Claims, 10 Drawing Sheets

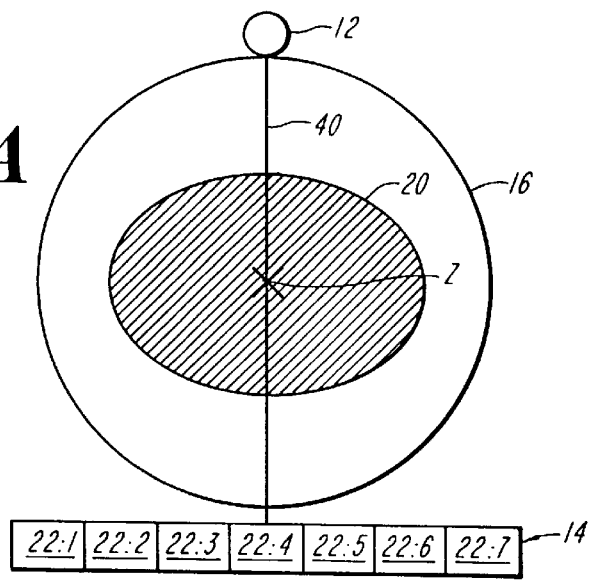
FIG. 9A
(PRIOR ART)
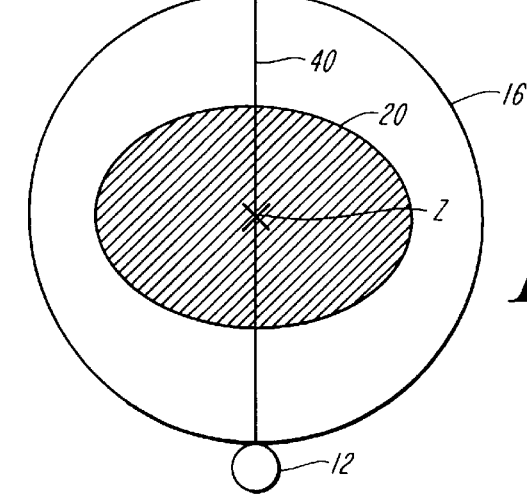
FIG. 9B
(PRIOR ART)
FIG. 10
(PRIOR ART)

STREAK SUPPRESSION FILTER

APPARATUS AND METHOD FOR COMPUTED TOMOGRAPHY SCANNING USING HALFSCAN RECONSTRUCTION WITH ASYMMETRIC DETECTOR SYSTEM

RELATED APPLICATIONS

This application is a continuation-in-part of allowed copending U.S. application Ser. No. 08/829,062 which was filed on Mar. 31, 1997, which is a continuation of U.S. application Ser. No. 08/759,368, filed on Nov. 27, 1996, now abandoned.

BACKGROUND OF THE INVENTION

FIG. 1 shows an axial view of a typical third generation computed tomography (CT) scanner 10 which includes an X-ray source 12 and an X-ray detector system 14 secured to diametrically opposite sides of an annular-shaped disk 16. The disk is rotatably mounted within a gantry support (not shown) so that during a scan, the disk continuously rotates about a Z-axis which is normal to the plane of the page in FIG. 1 and intersects the scanning plane at the mechanical center of rotation 18 of the disk, which corresponds to the "isocenter" of the reconstructed image. During scanning, X-rays pass from the source 12 through an object, such as a patient 20, positioned on a patient table 56 within the opening of the disk to the detector system 14.

The detector system 14 typically includes an array of individual detectors 22 disposed as a single row in the shape of an arc of a circle having a center of curvature at the point 24, referred to as the "focal spot", where the radiation emanates from the X-ray source 12. The X-ray source and the array of detectors are positioned so that the X-ray paths between the source and each detector all lie in a "scanning plane" that is normal to the Z-axis. Since the X-ray paths originate from what is substantially a point source and extend at different angles to the detectors, the X-ray paths form a "fan beam" 26 that is incident on the detector array 14. Each X-ray incident on a single detector at a measuring instant during a scan is commonly referred to as a "ray", and each detector generates an output signal indicative of the intensity of its corresponding ray. Since each ray is partially attenuated by all the mass in its path, the output signal generated by each detector is representative of the density of all the mass disposed between that detector and the X-ray source, i.e., the density of the mass lying in the detector's corresponding ray path.

The output signals generated by the X-ray detectors are normally processed by a signal processing portion (not shown) of the CT system. The signal processing portion generally includes a data acquisition system (DAS) which filters the output signals generated by the X-ray detectors to improve their signal-to-noise ratio. Such a DAS is described for example in U.S. Pat. No. 4,547,893. The output signals generated by the DAS during a measuring interval are commonly referred to as a "projection" or a "view", and the angular orientation of the disk 16 and of source 12 and detector system 14 mounted on the disk 16 corresponding to a particular projection is referred to as the "projection angle".

FIG. 2 illustrates the orientation of the disk 16 and the X-ray source 12 and detector system 14 mounted to the disk for generation of a fan beam data point $P_f(\beta,\gamma)$ at a projection angle of $\beta$ and a detector angle $\gamma$. A center line 40, which is used to define reference orientations, extends from the focal spot of the X-ray source 12 through the Z-axis at the mechanical center of rotation 18. The projection angle $\beta$ is defined as the angle between a vertical axis and center line 40. Each individual detector in system 14 has an associated detector angle $\gamma$ that is also defined with respect to center line 40. By definition, center line 40 intersects detector system 14 at a reference detector angle $\gamma$ of 0°. A symmetric detector system 14, as shown in FIG. 2, extends from a detector angle of $-\gamma_m$ to $+\gamma_m$. As will be discussed in greater detail below, an asymmetric detector system may be said to extend from a detector angle of $-\gamma_m+\alpha$ to $+\gamma_m$. A fan beam projection $P_f(\beta,\gamma)$ generated by symmetric detector system 14 includes the set of data points $P_f(\beta,\gamma)$ generated by all the detectors at detector angles from $-\gamma_m$ to $\gamma_m$ for the projection angle $\beta$.

During a scan, the disk 16 rotates smoothly and continuously around the object being scanned allowing the scanner 10 to generate a set of projections $P_f(\beta,\gamma)$ at a corresponding set of projection angles $\beta$. In a conventional scan, the patient remains at a constant Z-axis position during the scan, whereas in a helical (or spiral) CT scan, the patient is translated along the Z-axis while the disk is rotated about the patient. Alternatively, the patient can remain stationary and the disk translated along the Z-axis while being rotated about the patient. FIG. 3A illustrates the data collected during a conventional scan, and FIG. 3B illustrates the data collected during a helical scan. As shown in FIG. 3A, if the X-ray source 12 and detector system 14 are rotated about an object 20 while the object 20 remains at a fixed Z-axis location, the scanning planes associated with all the projections collected by detector system 14 will all lie in a common "slice plane" 50. As shown in FIG. 3B, if the object 20 is continuously translated in the direction of the Z-axis while the disk is rotated about the object 20, none of the scanning planes will be coplanar and thus lie in a common slice plane. Rather, the scanning plane associated with each projection will lie at a unique position along the Z-axis at a locus point on a helical set of loci. FIG. 3B illustrates the Z-axis coordinate of the scanning planes corresponding to helical projection angles in the interval (0,10π). Since the value of each projection depends on the Z-axis location of the patient, each projection may be considered a function of two variables, $\beta$ and z.

Since the patient remains at a constant Z-axis position during a conventional scan, this type of scanning is commonly referred to as "Constant Z-axis position scanning" or CZA scanning. In helical scanning, the projections $P_f(\beta,\gamma)$ are normally acquired such that z is linearly related to the view angle $\beta$ so that $z(\beta)=c\beta$, where c is a constant. This form of helical scanning is often referred to as Constant Speed Helical (CSH) scanning.

Using well known algorithms, such as the inverse Radon transform, a tomogram may be generated from a set of projections that all share the same scanning plane, and this common scanning plane as mentioned above is referred to as the "slice plane". A tomogram is representative of the density of a two dimensional "slice" along the slice plane of the object being scanned. The process of generating a tomogram from the projections is commonly referred to as "filtered back projection" or "reconstruction", since the tomogram may be thought of as being reconstructed from the projection data. The signal processing portion of a CT scanner normally includes a back projector for generating the tomograms from the projections.

In CZA scanning, all the projections share a common scanning plane, so these projections may be applied directly to the back projector for generation of a tomogram. In CSH scanning, each projection has a unique scanning plane located at a unique Z-axis coordinate, so CSH projections may not be applied directly to a back projector. However, as is well known, the data collected during a CSH scan may be interpolated in various fashions to generate a set of interpolated projections that do all share a common scanning plane extending normal to the Z-axis. Each interpolated projection, for example, may be generated by combining two projections taken at equivalent projection angles and at different Z-axis positions. These interpolated projections may be treated as CZA data and may be applied to a back projector to generate a tomogram.

CSH scanning disadvantageously requires some form of interpolation to generate a tomogram, and tomograms generated by CSH scanning therefore tend to be characterized by image artifacts. Also, since the CSH scan projection data, which is collected over an interval of Z-axis locations, is combined to generate the interpolated CZA scan data, tomograms generated during CSH scanning have a wider effective "slice plane width" than tomograms generated by CZA scanning. However, CSH scanning advantageously permits rapid scanning of a large volume of a patient. For example, in a time interval short enough to permit a patient to comfortably hold his or her breath and thereby remain relatively motionless, a CSH scan may collect enough data to fully scan an entire organ such as a kidney. In practice, the disk may, for example, be rotated on the order of $40\pi$ radians (i.e., 20 complete revolutions) during a single helical scan, and the data collected may be used to generate tomograms at a plurality of slice planes.

A tomogram may be reconstructed from a set of fan beam projections $P_f(\beta,\gamma)$ where $\beta$ is in the range $(0,\beta_{max})$. The choice of $\beta_{max}$ depends in part of the desired signal-to-noise ratio of the tomogram and in part on the desired slice plane width of the tomogram. Due to the rotational nature of CT scanners, the ray used to measure the data point $P_f(\beta,\gamma)$ is coincident with the ray used to measure the data point $P_f(\beta+2\pi,\gamma)$. So, in the absence of patient motion in a direction parallel to the Z-axis, projection data is periodic with period $2\pi$, and the data point $P_f(\beta,\gamma)$ equals the data point $P_f(\beta+2\pi,\gamma)$. One method of generating a tomogram from CZA scan data uses $\beta_{max}$ equal to $2\pi$. Since the disk 16 rotates completely around the patient, this type of scanning is often referred to as "fullscan". It is unnecessary to set $\beta_{max}$ greater than $2\pi$, since due to the periodicity of the projection data, this will result in collecting redundant data. However, such redundant data may be collected and can be used to improve the signal-to-noise ratio of a tomogram.

In addition to the above-described fullscan periodicity or redundancy, CT scanners also have an associated "halfscan" redundancy that is described by the following Equation (1).

$$P_f(\beta,\gamma)=P_f(\beta+\pi-2\gamma,-\gamma) \quad (1)$$

Equation (1) is true in the absence of patient motion because the ray used to measure the data point $P_f(\beta,\gamma)$ is coincident and antiparallel to the ray used to measure the data point $P_f(\beta+\pi-2\gamma,-\gamma)$. The rays are "antiparallel" because the relative positions of the X-ray source and detector are reversed. Known CT "halfscan" techniques use Equation (1) to permit generation of a tomogram from a set of CZA fan beam projections collected with $\beta_{max}$ equal to $\pi+2\gamma_m$. However, such a halfscan tomogram will have a lower signal-to-noise ratio than a fullscan tomogram where $\gamma_{max}$ equals $2\pi$.

Helical Interpolative, or HI scanning, is a scanning method that applies the above-described fullscan technique to CSH scanning. In HI scanning, projections are acquired for $\beta$ in the range of $(0,4\pi)$ while the patient is continuously translated along the Z-axis. This data is then used to approximate a set of CZA scan data for $\beta$ in the range of $(0,2\pi)$ by linearly interpolating data on each of the opposite sides of a slice plane located at the Z-axis position corresponding to a helical projection angle of $2\pi$. A fullscan filtered backprojection algorithm then generates a tomogram from this approximated CZA scan data.

In HI scanning, the data point $P_f(\beta_1,\gamma_1)$, which is the data point that would result from CZA scanning at Z-axis location $z_{sp}$, is estimated by linear interpolation according to the following Equation (2).

$$P_f(\beta_1,\gamma_1)=w_1P_f(\beta_1,\gamma_1)+w_2P_f(\beta_2,\gamma_2) \quad (2)$$

where $\beta_2=\beta_1+2\pi$, and $\gamma_1=\gamma_2$. The interpolation weights $w_1$ and $w_2$ of Equation (2) are given by the following Equation (3).

$$w_1 = \frac{\beta_2 - \beta_{sp}}{\beta_2 - \beta_1} \quad (3)$$

$$w_2 = \frac{\beta_{sp} - \beta_1}{\beta_2 - \beta_1}$$

One possible reconstruction method is to perform the interpolation of Equation (2) prior to filtered backprojection of the data, producing a data set with $z=z_{sp}$ and $\beta$ in the interval $(0,2\pi)$. Since filtered backprojection is linear, an alternative is to multiply the CSH scan data by interpolation weights $w(\beta,\gamma)$ and perform filtered backprojection on the entire $(0,4\pi)$ CSH scan data set. The latter method has some computational advantages since it permits pipelining of the reconstruction process and this method will be assumed for all helical algorithms subsequently presented herein. The weights $w(\beta,\gamma)$ for this method may be derived by substituting the relations $\beta_2=\beta_1+2\pi$ and $\gamma_1=\gamma_2$ into the above Equation (3) and are given by the following Equation (4).

$$w(\beta,\gamma) = \begin{cases} \frac{\beta}{2\pi} & 0 \leq \beta \leq 2\pi \\ \frac{4\pi - \beta}{2\pi} & 2\pi \leq \beta \leq 4\pi \end{cases} \quad (4)$$

The weights $w(\beta,\gamma)$ are continuous everywhere and go to zero at $\beta=0$ and $\beta=4\pi$, and go to unity at $\beta=2\pi$.

In addition to HI scanning, other techniques are known that require $4\pi$ of helical projection data to generate a tomogram, and these techniques shall be referred to herein as "helical fullscan techniques". Helical fullscan techniques are advantageous because they are relatively simple and straightforward to implement. However, helical fullscan techniques are disadvantageous because they require $4\pi$ of data to generate a single tomogram, and such tomograms are therefore characterized by relatively wide slice planes.

Helical Halfscan, or HH, scanning is a scanning method that applies the above-described halfscan techniques to CSH scanning. HH scanning advantageously permits generation of a tomogram with less than $4\pi$ of projection data. In HH scanning, CSH scan data is acquired for $\beta$ in the range $(0,2\pi+4\gamma_m)$. CZA scan data for $\beta$ in the range $(0,\pi+2\gamma_m)$ is approximated by linear interpolation of data on opposite sides of a slice plane located at the Z-axis position corresponding to a CSH scan projection angle of $\beta_{sp}=\pi+2\gamma_m$. A known halfscan filtered backprojection algorithm then generates a tomogram from this approximated CZA scan data. The advantage of HH scanning over the above-discussed helical fullscan techniques is that HH scanning uses fewer views, and therefore less patient motion, to reconstruct each tomogram. So the effective slice width of a HH scan tomogram is smaller than that of a helical fullscan tomogram.

FIG. 4 shows the Radon space (β vs. γ) for the data used by a HH scan to generate a single tomogram, and FIG. 4 also illustrates the Z-axis location corresponding to each projection angle β (along the vertical axis). The data shown in FIG. 4 is used to generate a tomogram having a slice plane, or Z-axis location, corresponding to the CSH projection angle of $\beta_{sp}=\pi+2\gamma_m$. In the absence of patient translation (i.e., in a CZA scan), regions 1–4 of the Radon space as illustrated in FIG. 4 would provide sufficient data to reconstruct a single tomogram using known halfscan techniques. Similarly, in the absence of patient translation, regions 5–8 would provide sufficient data to reconstruct a single tomogram. In HH, the data below the slice plane (i.e., regions 1–4) is combined with the data above the slice plane (i.e., regions 5–8) to approximate CZA data for regions 1–4 at the slice plane.

In FIG. 4, regions including redundant data are similarly striped, where redundant data are defined as data that are acquired along coincident rays (either parallel or antiparallel), and would therefore be identical in the absence of patient motion. So, regions 1, 4, and 7 are redundant; regions 2, 5, and 8 are redundant; and regions 3 and 6 are redundant. In HH, similarly striped regions are combined to approximate a set of CZA data in regions 1 through 4. Methods of combining the data are described in detail in "Computed tomography scanning with simultaneous patient translation," by Carl R. Crawford and Kevin F. King, Med. Phys. 17 (6), Nov/Dec 1990. The reconstruction weights for HH scanning are given by the following Equation (5).

$$w_{HH}(\beta,\gamma) = \begin{cases} 0 & 0 \leq \beta \leq 2\gamma_m - 2\gamma \\ \dfrac{\beta + 2\gamma - 2\gamma_m}{\pi + 2\gamma} & 2\gamma_m - 2\gamma \leq \beta \leq \pi + 2\gamma_m \\ \dfrac{2\pi - \beta - 2\gamma + 2\gamma_m}{\pi - 2\gamma} & \pi + 2\gamma_m \leq \beta \leq 2\pi + 2\gamma_m - 2\gamma \\ 0 & \pi + 2\gamma_m - 2\gamma \leq \beta \leq 2\pi + 4\gamma_m \end{cases} \quad (5)$$

Helical Extrapolative, or HE scanning, is another scanning method that applies halfscan techniques to CSH scanning. In HE scanning, CSH scanned data is collected for β in the range of $(0, 2\pi)$. CZA scanned data for β in the range of $(0, \pi + 2\gamma_m)$ is interpolated and extrapolated from this CSH scanned data and a known halfscan technique is then used to generate a tomogram from this approximated CZA scanned data. FIG. 5 illustrates the Radon space for the data used by HE scanning to generate a single tomogram at a slice plane corresponding to the CSH projection angle of $\beta_{sp}=\pi$. In the absence of patient motion (i.e., in a CZA scan), the regions 1, 2, and 3 illustrated in FIG. 5 would provide sufficient data to reconstruct a single tomogram using known halfscan techniques. Similarly, in the absence of patient motion, the regions 4, 5, and 6 would also provide sufficient data to reconstruct a single tomogram. In HE scanning, the data in regions 1–3 is combined with the data in regions 4–6 to approximate CZA data for regions 1–3 at the slice plane.

Regions 2 and 5 illustrated in FIG. 5 are redundant, and data in these regions are interpolated to approximate CZA data for region 2. The data in regions 1 and 4 are also redundant. Since regions 1 and 4 both lie on the same side of the slice plane, the CZA scanned data for region 1 are generated by extrapolating (rather than interpolating) the CSH scanned data in regions 1 and 4. Similarly, the data in regions 3 and 6 are redundant and lie on the same side of the slice plane, so the CZA scanned data for region 3 are generated by extrapolating the CSH scan data in regions 3 and 6. The advantage of HE scanning over the above-discussed HH scanning method is that HE scanning uses fewer views and therefore less patient Z-axis translation to reconstruct each tomogram. So, the effective slice width of a HE scan tomogram is smaller than that of a HH scan tomogram. However, HE scanning requires some extrapolation to generate the CZA scanned data for regions 1 and 3, whereas HH scanning relies entirely on interpolation. So to the extent that interpolation is more accurate than extrapolation, HH scan may generate more accurate tomograms.

The above-referenced article entitled "Computed tomography scanning with simultaneous patient translation," describes HE scanning in detail. The weights for the HE scanning method are given by the following Equation (6).

$$w_{HE}(\beta,\gamma) = \begin{cases} \dfrac{\beta + 2\gamma}{2\pi + 2\gamma} & 0 \leq \beta \leq \pi - 2\gamma \\ \dfrac{2\pi - \beta - 2\gamma}{\pi - 2\gamma} & \pi - 2\gamma \leq \beta \leq 2\pi \end{cases} \quad (6)$$

The weighting function $w_{HE}(\beta,\gamma)$ is discontinuous in γ along the line $\beta=\pi-2\gamma$, except at $\gamma=0$ and there is an inconsistency in the discretely sampled weighted projection data leading to streaks which appear to originate from the first view and become deeper for greater distances away from the isocenter. The discontinuity can be eliminated by feathering $w_{HE}(\beta,\gamma)$ across the line $\beta=\pi-2\gamma$.

The procedure for feathering may be understood as a general procedure for smoothing a discontinuity in a function $w(x)$ at a location $x_0$ where $w(x)$ is given by the following Equation (7)

$$w(x) = \begin{cases} w_1(x) & x < x_0 \\ w_2(x) & x \geq x_0 \end{cases} \quad (7)$$

and where $w_1(x_0) \neq w_2(x_0)$ so that $w(x)$ is discontinuous at $x=x_0$. The feathering algorithm smooths the discontinuity by extending $w_1(x)$ and $w_2(x)$ by a distance $d/2$ on either side of $x=x_0$ and redefining $w(x)$ according to the following Equation (8)

$$w(x) = \begin{cases} w_1(x) \text{ for } x \leq x_0 - \dfrac{d}{2} \\ w_1(x)\left[1 - f\left(\dfrac{x-x_0}{d} + \dfrac{1}{2}\right)\right] + w_2(x)f\left(\dfrac{x-x_0}{d} + \dfrac{1}{2}\right) \\ \text{for } x_0 - \dfrac{d}{2} \leq x \leq x_0 + \dfrac{d}{2} \\ w_2(x) \text{ for } x \geq x_0 + \dfrac{d}{2} \end{cases} \quad (8)$$

where the function $f(x)$ is equal to zero for x less than zero, and is equal to one for x greater than one, and is smooth and continuous over the interval $0<x<1$. An exemplary function $f(x)$ for use in the feathering algorithm is given by the following Equation (9).

$$f(x) = \begin{cases} 0 & x < 0 \\ 3x^2 - 2x^3 & 0 \leq x \leq 1 \\ 1 & x > 1 \end{cases} \quad (9)$$

The above-referenced article entitled "Computed tomography scanning with simultaneous patient translation," reported that a feathering distance d equal to ten channels, i.e., ten times the length of a single detector, is sufficient for operation of the HE scanning method.

In addition to HH and HE scanning, other techniques are known for generating a tomogram from less than 4π of helical projection data, and such techniques shall be referred to herein as "helical halfscan techniques". Some helical halfscan techniques are disclosed for example in "A General Approach to the Reconstruction of X-ray Helical Computed Tomography," Jiang Hsieh, Med. Phys. 23 (2), February 1996.

FIG. 6 illustrates the geometry of a CT scanner having an asymmetric detector system 14. This detector system includes a symmetric portion 14a extending from detector angle $-\gamma_m+\alpha$ to $\gamma_m-\alpha$, and an asymmetric portion 14b extending from detector angle $\gamma_m-\alpha$ to $\gamma_m$, where $\alpha$ is the angular extent of the asymmetric portion ($\alpha>0$). Detector system 14 may also be thought of as not including a portion 14c extending from detector angle $-\gamma_m$ to $-\gamma_m+\alpha$. If detector system 14 did include the missing portion 14c, then the detector system would be symmetric. A fan beam projection generated by asymmetric detector system 14 includes the set of data points $P_f(\beta,\gamma)$ generated by all the detectors at detector angles from $-\gamma_m+\alpha$ to $\gamma_m$.

Such asymmetric detector systems are often used in CT scanners so as to increase the field of view (FOV) of the scanner without significantly increasing the cost of the detector system and associated DAS. The FOV of a scanner is determined by the angular extent of the detector system. For example, the FOV of a scanner using the symmetric detector system illustrated in FIG. 2 is equal to $2\gamma_m$, and the FOV of a scanner using the asymmetric detector system illustrated in FIG. 6 is equal to $2\gamma_m-\alpha$. This suggests that the FOV provided by an asymmetric detector system is smaller than the FOV ($2\gamma_m$) provided by a comparable symmetric detector system. However, alternative symmetric and asymmetric detector systems are properly compared by considering the angular extent of the symmetric portion of the asymmetric detector system to be equal or nearly equal to the angular extent of the alternative symmetric detector system, i.e., the $\gamma_m-\alpha$ portion of the asymmetric detector system is equal or nearly equal to $\gamma_m$ of the alternative symmetric detector system. So use of the asymmetric detector system effectively increases the FOV of the scanner by $\alpha$.

Another advantage of asymmetric detector systems relates to the contribution that each individual detector makes to a tomogram. As is well known, the importance of each detector in terms of its contribution to tomograms decreases with increasing detector angle. So it is reasonable to eliminate half the detectors having a detector angle the absolute value of which is greater than a predetermined threshold. By way of example, the Anatom scanner, which is manufactured by the Analogic Corporation of Peabody, Mass., uses a detector system that includes three hundred eighty four individual detectors. In this detector system, each individual detector subtends a detector angle of 0.125°, $\gamma_m$ is equal to 28.843°, and $\alpha$ is equal to 9.687°. Although such asymmetric detector systems are popular, their use complicates the process of generating helical scans.

The above Equation (1), which describes halfscan redundancy, is not true for the asymmetric portion of the detector array, and this prevents the use of helical halfscan techniques such as HH and HE scanning with asymmetric detector arrays. So for prior art CT scanners including asymmetric detector arrays, helical scanning may be performed using a helical fullscan technique (such as HI scanning) and data collected from the entire array, or alternatively, data from the asymmetric portion may be ignored and helical scanning may be performed using a helical halfscan technique such as HH or HE scanning. However, it would be advantageous to be able to perform helical scanning using a helical halfscan technique such as HH or HE scanning and also use all the data collected by an asymmetric detector array.

Another problem with prior art helical scanning techniques relates to the "quarter detector offset" used in many CT scanners. A CT scanner using a quarter detector offset is described for example in U.S. patent application Ser. No. 08/191,428, entitled, X-RAY TOMOGRAPHY SYSTEM FOR AND METHOD OF IMPROVING THE QUALITY OF A SCANNED IMAGE, filed on Feb. 3, 1994, (Attorney Docket No. ANA-044). In general, in a CT scanner using a quarter detector offset, the center line 40 as shown in FIG. 2, which passes through the focal spot of the X-ray source 12 and the Z-axis, does not intersect the center of one of the detectors in the detector system 14. Rather, it intersects one of the detectors, which shall be referred to herein as the "central detector", at a location slightly offset from the central detector's center. This insures that the ray measured by the central detector at a projection angle $\beta$ is not coincident with the ray measured by that detector at a projection angle of $\beta+\pi$. Rather, the two rays are offset from one another. As is well known, using such a quarter detector offset increases the amount of data collected by a scanner during a 360° rotation of the disk by increasing the number of unique sampling points. However, use of a quarter detector offset complicates the process of CSH scanning, regardless of whether the detector system used is symmetric or asymmetric.

As is well known, the fan beam projection data collected during a CT scan is often "rebinned" or "reordered" to form reordered projection data, such that all the rays used to generate a single reordered projection are mutually parallel. In systems using a quarter detector offset, the reordered projections are typically "interleaved" to generate parallel beam projection data. FIG. 7A illustrates some of the individual rays in a fan beam projection 100 taken at a fan beam projection angle of zero degrees, and FIG. 7B illustrates some of the individual rays in a parallel beam projection 102 taken at a parallel beam projection angle of zero degrees. As shown, none of the rays in the fan beam projection 100 are parallel to one another, while all of the rays in the parallel beam projection 102 are mutually parallel. Since all of the rays emanate from the focal spot of the X-ray source 12 to form a fan beam, the CT scanner may not generate all the rays of a parallel beam projection simultaneously. However as is well known, the fan beam projection data may be reordered and interleaved to generate parallel beam projections. Known fullscan and halfscan parallel beam reconstruction algorithms may generate a tomogram from CZA parallel beam projections $P_p(\beta,\gamma)$ for $\beta$ in the range $(0,2\pi)$ and $(0,\pi)$, respectively.

FIGS. 8A and 8B illustrate a method of generating the reordered projections. FIGS. 8A and 8B show the positions of X-ray source 12 and detector system 14 during generation of two successive fan beam projections. FIGS. 8A and 8B show detector system 14 as including eight individual detectors, four of which are labeled 22:1, 22:2, 22:3, and 22:4. Most detector systems include hundreds of detectors, and as stated above, the detector system used in the Anatom scanner includes three hundred eighty four detectors. However, for convenience of illustration, the eight detector system shall now be discussed. During a scan, as shown in FIGS. 8A and 8B, X-ray source 12 and detector system 14 rotate in a counter clockwise direction about the Z-axis, the latter extending perpendicular to the sheet of the drawing. During the first projection, shown in FIG. 8A, a ray 114 is incident on a detector 22:4 (i.e., the detector in the fourth channel of detector system 14). During the next projection, shown in FIG. 8B, a ray 116 is incident on detector 22:3 (i.e., the detector in the third channel of detector system 14). When the spacing between the individual detectors is matched to the amount of disk rotation between generation of successive fan beam projections, the ray 114 is parallel to, and slightly offset from, ray 116. When this basic relationship is true for all detectors and all fan beam projections, any two rays incident on adjacent detectors during successive fan beam projections are parallel and are offset from each other. As was stated above, in the Anatom scanner, the individual detectors are spaced apart by 0.125°, and consequently, in that scanner, successive projections are separated by a projection angle that is also equal to 0.125°. This allows the fan beam data collected by that scanner to be reordered into reordered projections.

When a symmetric detector system 14 includes a quarter detector offset, the reordered parallel beam projections may then be interleaved to generate interleaved parallel beam projections. Each interleaved parallel beam projection is generated by combining the data from two reordered projections taken at reordered projection angles that are 180° apart to form a single denser projection. FIGS. 9A and 9B illustrate the spatial relationship between X-ray source 12, a cross section of patient 20, and symmetric detector system 14 for projection angles of zero and 180 degrees, respectively. In FIGS. 9A and 9B, symmetric detector system 14 is once again shown for convenience of illustration as containing seven individual detectors. The illustrated detector system 14 has a quarter detector offset so that the center liner 40 which extends from the focal spot of the X-ray source 12 through the Z-axis does not intersect the center of the central detector 22:4. Rather, the center line 40 intersects the central detector 22:4 at a point that is offset from the center by one quarter of the detector's width.

FIG. 10 illustrates the spatial relationship between symmetric detector system 14 at projection angles of zero and 180 degrees, and the rays 120, 122, 124 incident on three of the detectors. Because of the quarter detector offset between symmetric detector system 14 and center line 40, the detector system 14 at a projection angle of zero degrees is offset from the detector system 14 at 180 degrees. Consequently, the ray 120 that is incident on the sixth channel detector 22:6 for a projection angle of 180 degrees falls precisely between the rays 122 and 124 that are incident on detectors 22:2 and 22:3, respectively, for a projection angle of zero degrees. The interleaved set of data provided by the detector system at 180 degrees is thus displaced by one-half a detector width relative to the set of data provided by the detector system at zero degrees. In this example, detector 22:6 may be thought of as a "center" detector and detectors 22:2 and 22:3 may be thought of as "opposite-adjacent" detectors. At each projection angle, each detector measures the integral of the density of mass along a particular ray path, and in general, the ray paths used by the opposite-adjacent detectors are closer to the ray path used by the center detector than are the ray paths used by any other detectors, e.g., the ray path used by detectors 22:2, 22:3 at a projection angle of zero degrees are closer to the ray path used by detector 22:6 at a projection angle of 180 degrees than are the ray paths used by detectors 22:5, 22:7 at a projection angle of 180 degrees. Any two reordered projections separated by 180 degrees may be interleaved using this relationship between center and opposite-adjacent detectors to form a single denser parallel beam projection.

A single interleaved parallel beam projection generated by a symmetric detector system may be represented as a set of data points D:1, D:2, D:3, . . . , D:N. In this representation, all of the odd data points, e.g., D:1 and D:3, are contributed by a reordered projection taken at a reordered projection angle of $\beta$, and all of the even data points, e.g., D:2 and D:4, are contributed by a reordered projection taken at a reordered projection angle of $\beta+\pi$.

Two reordered projections generated at reordered projection angles of p and $\beta$ and $\beta+\pi$ by an asymmetric detector system 14, such as the one shown in FIG. 6, may also be interleaved to generate a single interleaved parallel beam projection. However, the procedure for interleaving data collected by an asymmetric detector system is different from the procedure used for data collected by a symmetric detector system. This is so because the data required for interleaving the asymmetric portion 14b could only be collected by the missing portion 14c shown in FIG. 6. So when an asymmetric detector system 14 is used, the resulting interleaved parallel beam projections include a central region and two exterior regions. In the central region, the data points are structured identically to projections generated by symmetric detector systems and every other data point is contributed by a different reordered projection. In one of the exterior regions, all of the data points are contributed by the reordered projection generated at a reordered projection angle of $\beta$, and in the other exterior region, all of the data points are contributed by the reordered projection generated at a reordered projection angle of $\beta+\pi$. Since the data points in the exterior regions are not interleaved, the angular spacing between adjacent data points in the exterior regions is double the angular spacing between adjacent data points in the central region.

A single interleaved parallel beam projection generated by an asymmetric detector system may be represented as a set of data points D:i for all integers i from one to $N_m$, where $N_m$ equals $2N_s$ plus $2N_a$, where $N_s$ equals the number of detectors in the symmetric portion 14a of the detector system, and where $N_a$ equals the number of detectors in the asymmetric portion 14b of the detector system. In this representation, all the data points D:i are undefined for i=2j+1 and for i=$N_m$−2j for all integers j greater than or equal to zero and less than or equal to $N_a$−1. These undefined data points are the odd data points in one of the exterior regions and the even data points in the other exterior region. These undefined data points could have only been collected by the missing portion 14c of the detector system. In this representation, all of the (defined) odd data points are contributed by a reordered projection generated at a reordered projection angle of $\beta$ and all of the (defined) even data points are contributed by reordered projection generated at a reordered projection angle of $\beta+\pi$.

Hereinafter, parallel beam projections taken at a parallel beam projection angle of $\beta$ shall be referred to as including a set of "odd data points" and a set of "even data points", and the term "odd data points" shall refer to data points measured at a reordered projection angle $\beta$, and the term "even data points" shall refer to data points measured at a reordered projection angle of $\beta+\pi$. Further, the term "odd data points" shall also refer to the data points in the fan beam projections that may be reordered and interleaved to form the odd data points of a parallel beam projection, and the term "even data points" shall also refer to the data points in the fan beam projections that may be reordered and interleaved to form the even data points of a parallel beam projection.

In the central region of an interleaved parallel beam projection, the ray path used to generate the $i^{th}$ data point D:i is closer to the ray paths used to generate the adjacent data points D:i−1 and D:i+1 than to any other ray paths.

However, the difference between the measurement times of adjacent data points (e.g., D:i and D:i−1) is much greater than the difference between the measurement times of alternate data points (e.g., D:i and D:i−2). For example, if T:i represents the time that a data point D:i is measured, then T:i minus T:i−1 is much greater than T:i minus T:i−2. This is true because all of the even points of a single parallel beam projection are contributed by a single reordered projection (and all the data points of a reordered projection are generated by a set of adjacent fan beam projections), however, adjacent data points in the central region of a parallel beam projection are contributed by two different reordered projections generated approximately 180° apart from one another. So the measurement times of such adjacent data points are separated by the time required for the disk to rotate approximately 138°.

In the absence of patient translation motion, i.e., in a CZA scan during which the patient is not moved, the portions of the patient measured by adjacent data points of the central region of a parallel beam projection are physically proximal to one another. However, in the central region of a parallel beam projection generated from CSH scan data, the portions of the patient measured by adjacent data points are axially separated by a relatively large distance because the patient is translated a considerable distance in the direction of the Z-axis during the time required for the disk to rotate approximately 180°. This leads to a discrepancy between the even data points and the odd data points in every single parallel beam projection generated during a CSH scan. Further, there is an even larger discrepancy in the helical weights applied to even and odd data points. This is also true for halfscan weights. These discrepancies appear as high frequency noise in the projection data and complicate the process of generating tomograms from CSH data collected with offset detector systems.

In particular, this high frequency noise complicates the process of performing "isocenter interpolation" and also complicates the process of suppressing streak artifacts from tomograms generated from CSH scans. As is well known, isocenter interpolation refers to an interpolation process used to equalize the linear spacing between data points in a parallel beam projection. Prior art techniques of performing isocenter interpolation, and/or streak suppression do not function well when applied to CSH scan data, and tend to generate tomograms that are characterized by a relatively large amount of image artifacts. One prior art method of reducing these artifacts is to select a convolution kernel for filtered backprojection that includes a low-pass filter for suppressing the high frequency information caused by the quarter detector offset. While such a convolution kernel effectively suppresses some artifacts, it also has the unwanted consequence of reducing the resolution of the resulting tomogram.

In CZA scanning, fullscan acquisition involves collecting projections during rotation of the gantry through $2\pi$ radians. Rebinning of the fan beam projections to parallel and interleaving of offset projections produces a sampling spacing equal to twice that which can be achieved without interleaving. Halfscan acquisition, which is also known in the CT industry as partial or segment scanning, is performed using the minimum number of fan beam projections required to generate a set of parallel projections over $\pi$ radians.

In the symmetric portion of the asymmetric array, fan beam projections are acquired over an angle equal to $\pi$ radians plus the symmetric fan angle. Because insufficient projections are acquired to perform interleaving over the entire data set, the level of aliasing artifacts is higher than that found in a fullscan reconstruction. The noise level in the image also increases due to the reduced number of projections used in the reconstruction. The advantages of halfscan reconstruction include reduced scan times and reduced radiation dose. In addition, halfscan reconstruction can be used to reconstruct fullscan data that is corrupted by factors such as patient motion during a portion of the scan. In practice, it is possible to salvage a usable halfscan image from a data set that produces a useless image with fullscan reconstruction.

Dynamic scan data, which consist of views acquired during multiple rotations of the gantry, can be reconstructed using either a fullscan or a halfscan reconstruction technique. A temporal series of images is produced by reconstructing data collected at later times. It may be desirable to apply a halfscan reconstruction technique to dynamic scan data to increase the temporal resolution of the series of images over that obtained using fullscan reconstruction.

The quality of an image is further compromised when halfscan acquisition is used and the patient being scanned is oversized, that is, extends beyond the field-of-view of the scanner. In this case, artifacts are introduced into the image where portions of the patient outside the symmetric field-of-view of the scanner are scanned by the asymmetric portion of the array.

OBJECTS OF THE INVENTION

It is an object of the present invention to substantially reduce or overcome the above-identified problems of the prior art.

Another object of the present invention is to provide a method and apparatus for constant Z-axis scanning that can generate a tomogram from the data collected by an asymmetric detector system using a halfscan technique.

Another object of the present invention is to provide a method and apparatus for constant Z-axis scanning that can generate a tomogram from halfscan acquired data collected by an asymmetric detector system for the condition in which the subject being scanned extends beyond the field of view of the scanner.

Another object of the present invention is to provide a method and apparatus for constant Z-axis scanning for use with asymmetric detector arrays that use a detector offset.

Still another object of the present invention is to provide a method and apparatus for performing isocenter interpolation for data collected during a constant Z-axis scan.

Yet another object of the present invention is to provide a method of and apparatus for performing streak artifact suppression for data collected during a constant Z-axis scan.

SUMMARY OF THE INVENTION

These and other objects are provided by the method and apparatus of the invention for generating tomographic image data for an object. The invention includes a radiation source which directs radiation though the object and an array of detectors which receives radiation from the object to acquire fan beam projection data used to generate the image data. The array of detectors and the radiation source are preferably rotatable about a center of rotation in the object through a plurality of projection angles to acquire the fan beam projection data. The ends of the array of detectors define a fan angle having an apex defined by the radiation source. A line connecting the radiation source and the center of rotation of the object divides the fan angle into two partial non-equal fan angles, that is, the array of detectors is asymmetric. Each detector in the array can be viewed as defining a line which connects the detector and the radiation source. Each such line defines a detector angle φ with the line connecting the radiation source and the center of rotation in the object. The smaller of the partial fan angles can be referred to as $\phi_{MIN}$, and the larger of the partial fan angles can be referred to as $\phi_{MAX}$. In the present invention, each slice of image data is generated from a sub set of a complete set of fan beam projection data for the slice, where, for the purposes of the present invention, a complete set of fan beam projection data includes all of the fan beam projection data that is available from a complete 360° revolution of the radiation source and the array of detectors about the center of rotation in the object. In the present invention, the subset of data used to generate a slice contains less data than a complete set of available data.

In one embodiment, the invention provides an approach to halfscan reconstruction in constant Z-axis (CZA) scanning using fullscan acquisition. In another embodiment, the invention provides a halfscan reconstruction approach using CZA halfscan acquisition on an oversized patient, i.e., where the patient extends beyond the field of view of the array of detectors such that portions of the patient are missed in the asymmetric portion in the array of detectors. In either approach, data is manipulated and/or discarded (set to zero) using a data weighting approach. In one embodiment, two different weighting schemes are applied to the projection data. A first scheme is applied to the data acquired by detectors in the asymmetric portion of the array, and a second weighting scheme is applied to data acquired by detectors in the symmetric portion of the array. In general, in both weighting schemes, an unused portion of the complete set of fan beam projection data is identified and weights are set for that data such that the unused portion is set to zero and, therefore, is in effect discarded.

In halfscan reconstruction using CZA halfscan acquisition of an oversized patient, the unused portion of the data is defined as that portion of data acquired by the asymmetric portion of the array. In this case, the weighting scheme applied to the asymmetric portion of the array data is such that the data acquired by the asymmetric portion of the array is set to zero and in effect discarded. Hence, in the oversized patient case, identifying the unused portion of the fan beam projection data includes identifying unused detectors, namely, the detectors in the asymmetric portion of the array. In this case, a known approach to processing oversized patient data can be applied. For example, a linear ramp function can be applied in the asymmetric portion of the data such that the sharp edge between the symmetric portion and the end of the asymmetric portion is eliminated by a smooth ramp function.

Where halfscan reconstruction is applied to fullscan acquired CZA data, the weighting schemes are applied such that halfscan reconstruction is applied to the projection data acquired by the symmetric portion of the array and fullscan reconstruction is applied to the data acquired by the asymmetric portion of the array. In this case, identifying an unused portion of the data comprises, in the symmetric portion of the data, identifying a set of projection angles fewer than a complete revolution at which the data will be weighted to zero. In effect, identifying unused data involves identifying unused projection angles for the symmetric portion of the data. In one embodiment, the unused projection angles can be outside a range which spans an angle of π radians (one-half of a complete revolution) plus twice the symmetric partial fan angle $\phi_{MIN}$.

In one embodiment, a feathering approach is applied to blend the first and second weighting schemes. This is done to provide smooth image data. Linear blending and/or quadratic blending functions can be used and the blending scheme can be performed over angles subtended by ten detectors. The weights for both the first and second weighting schemes can correspond to halfscan reconstruction of data and fullscan reconstruction of data.

The halfscan reconstruction approach of the invention can be applied to dynamic scan data acquired by an asymmetric array. Fullscan data an be extracted from the dynamic scan data and the approach of the invention can be applied. An advantage of this approach is that the patient anatomy can extend into the asymmetric portion of the array without causing any significant degradation of the image.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE DRAWINGS

For a fuller understanding of the nature and objects of the present invention, reference should be had to the following detailed description taken in connection with the accompanying drawings in which the same reference numerals are used to indicate the same or similar parts wherein:

FIGS. 9A and 9B show simplified schematic, axial views of a prior art detector system at projection angles of 0° and 180°, respectively;

FIG. 10 shows the spatial relationship between the detector system of FIGS. 9A and 9B at projection angles of 0° and 180°;

DETAILED DESCRIPTION OF THE DRAWINGS

Figure 1:
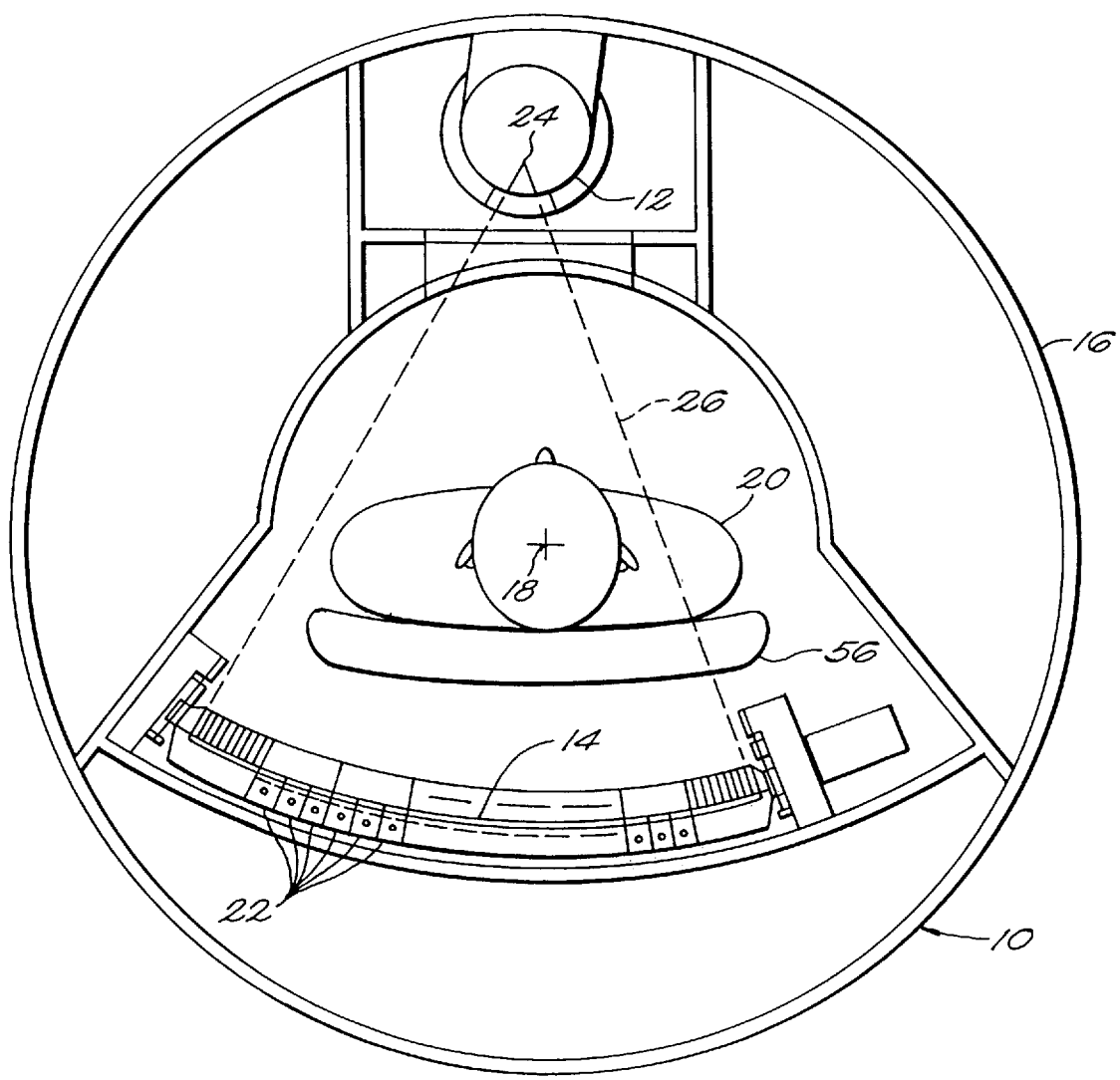
FIG. 1 shows an axial view of a prior art CT scanner.
Figure 2:
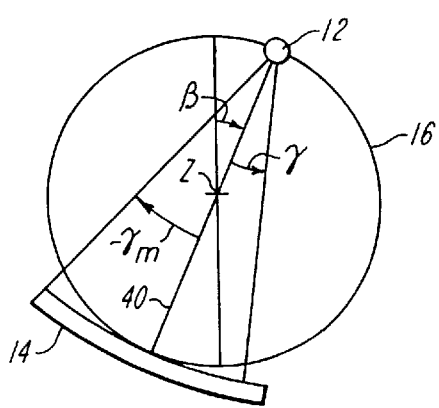
FIG. 2 is a simplified schematic, axial view of the CT scanner shown in FIG. 1 showing the orientations of the disk, X-ray source, and detector system for generation of a projection at a projection angle of β.
Figure 6:
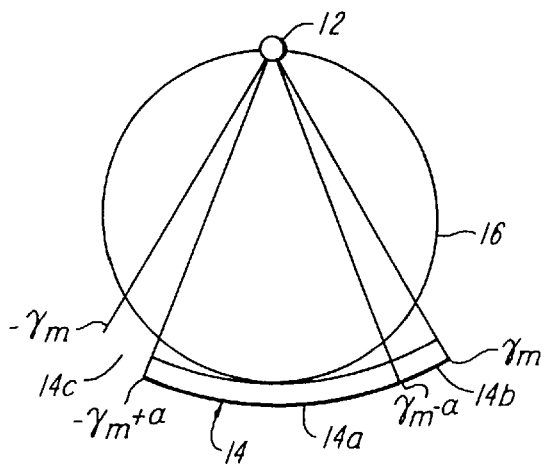
FIG. 6 is a simplified schematic axial view of a CT scanner having an asymmetric detector system.

The present invention provides improved methods and apparatus for generating tomograms from data collected during CSH scans. One improved method provided by the present invention is referred to herein as "Helical Asymmetric", or HA scanning. HA scanning assumes that an asymmetric detector array (e.g., such as the one shown in FIG. 6) is used to collect the projection data. In HA scanning, CSH data $P_f(\beta,\gamma)$ is acquired for $\beta$ in the range $(0,4\pi)$ and for $\gamma$ in the range $(-\gamma_m+\alpha,\gamma_m)$. HA scanning uses a helical fullscan technique (such as HI or some other helical fullscan technique) to process the CSH scan data collected by the asymmetric portion of the detector array, and uses a helical halfscan technique (such as HH scan, HE scan, or some other helical halfscan technique) to process the CSH scan data collected by the symmetric portion of the detector array. More specifically, HA scanning uses a helical fullscan technique to process the fan beam projection data points $P_f(\beta,\gamma)$ for $\gamma$ in the range $(\gamma_m-\alpha,\gamma_m)$ (i.e., the asymmetric portion) and $\beta$ in the range $(0,4\pi)$ so as to approximate CZA scan data for $\beta$ in the range $(0,2\pi)$ and $\gamma$ in the range $(\gamma_m-\alpha,\gamma_m)$. HA scanning also uses a helical halfscan technique to process the fan beam projection data points $P_f(\beta,\gamma)$ for $\gamma$ in the range $(-\gamma_m+\alpha,\gamma_m-\alpha)$ (i.e., the symmetric portion) and $\beta$ in the range $(2\pi-\psi/2,2\pi+\psi/2)$ (where $\psi$ is the extent of fan beam projections required for a halfscan helical technique, e.g., $\psi$ equals $2\pi+4\gamma_m$ for a HH scan and equals $2\pi$ for a HE scan) so as to approximate CZA scanned data for $\beta$ in the range $(2\pi-\psi/2,2\pi)$ and $\gamma$ in the range $(-\gamma_m+\alpha, \gamma_m-\alpha)$. HA scanning then uses the two sets of approximated CZA scanned data (i.e., one set generated from data collected by the asymmetric portion of the detector system, and another set generated from data collected by the symmetric portion of the detector system) to generate a single tomogram at a slice plane corresponding to the CSH projection angle of $2\pi$.

As those skilled in the art will appreciate, a tomogram may be generated from the data collected by the symmetric portion of the detector system using a helical halfscan technique. Similarly, another tomogram may also be generated from the data collected by the asymmetric portion of the detector system using a helical fullscan technique. The signal-to-noise ratio of these tomograms will in effect be limited because each tomogram is generated using only data collected by a limited portion of the detector system. HA scanning advantageously uses these two portions of data (i.e., the portions generated by the symmetric and asymmetric portions of the detector system) to generate a single tomogram having an improved signal-to-noise ratio. Since a helical halfscan technique is applied to the data collected by the symmetric portion of the detector system, the portion of the tomogram generated from this data has an associated slice plane width that is determined by the helical halfscan technique. Similarly, since a helical fullscan technique is applied to the data collected by the asymmetric portion of the detector system, the portion of the tomogram that is generated from this data has an associated slice plane width that is determined by the helical fullscan technique. So, HA scanning (1) advantageously minimizes the slice plane width of at least a portion of the tomogram, (2) advantageously permits reconstruction of a tomogram using all of the data collected by an asymmetric detector system, and (3) improves the signal-to-noise ratio of the reconstructed tomograms.

Figure 11:
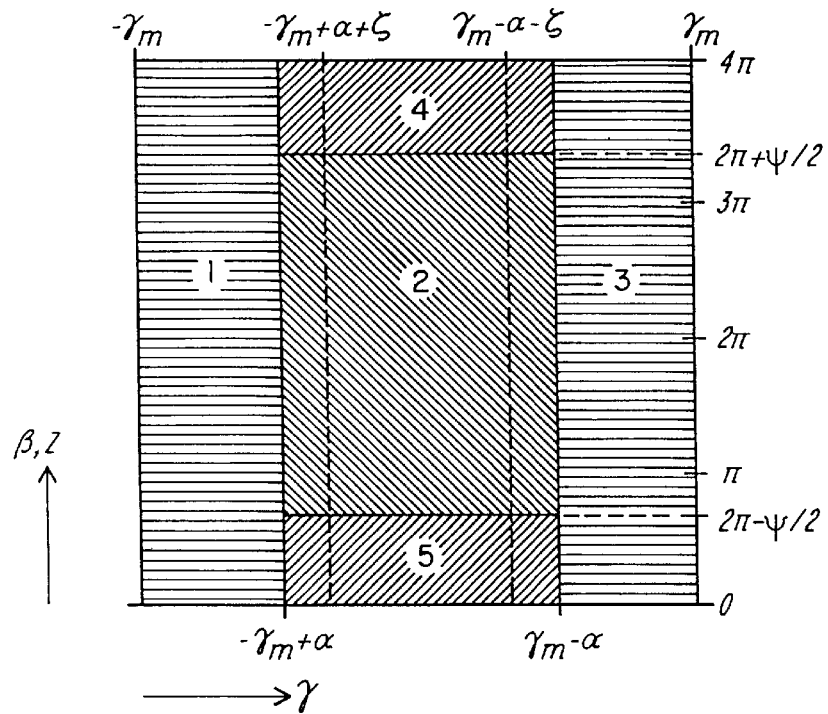
FIG. 11 is a graph of the Radon space used by a "Helical Asymmetric" (HA) scan according to the invention to generate a tomogram at a slice plane corresponding to a projection angle of $2\pi$.

FIG. 11 illustrates the Radon space for data used by a HA scan. When the data illustrated in FIG. 11 is collected with an asymmetric detector system of the type shown in FIG. 6, regions 2, 4, and 5 represent the data collected by the symmetric portion 14a of the detector system. Region 3 represents data collected by the asymmetric portion 14b of the detector system. Finally, region 1 represents data that would be collected by the missing portion 14c of the detector system, if such a portion were present. In a HA scan, a helical halfscan technique (e.g., a HH scan or HE scan) is applied to the data collected by the symmetric portion of the detector system (i.e., regions 2, 4, and 5), and a helical fullscan technique (e.g., HI scan) is applied to the data collected by the asymmetric portion of the detector system (i.e., region 3). Since the helical halfscan technique only requires CSH fan beam projection data with $\beta$ in the range $(2\pi-\psi/2,2\pi+\psi/2)$, the data in region 2 is sufficient to generate a tomogram, and the data in regions 4 and 5 may be discarded. Discarding the data in regions 4 and 5 effectively reduces the slice plane width of the part of the tomogram that is generated by the symmetric portion of the detector array.

One method of implementing a HA scan is to multiply the data in the Radon space (as illustrated in FIG. 11) by a set of weights prior to performing a filtered backprojection. The weights for region 1 are zero, since region 1 represents data that is not actually collected by the asymmetric detector system. The weights for regions 4 and 5 are also zero, since the data in these regions are preferably discarded so as to reduce the slice plane width for at least a portion of the tomogram. The weights for region 2 are determined by the helical halfscan technique and the weights for region 3 are determined by the helical fullscan technique. When scanning technique HI is used as the helical fullscan technique, the weights for region 3 are given by the above-listed Equation (4), and when a HH or HE scanning technique is used for the helical halfscan technique, the weights for region 2 are determined in part by the above-listed Equations (5) or (6), respectively. Equations (5) and (6) describe the weights $w_{HH}(\beta,\gamma)$ and $w_{HE}(\beta,\gamma)$, for a HH and HE scanning techniques, respectively, for $\beta$ in the interval $(0,\psi)$. However, in region 2, $\beta$ extends over the interval $(2\pi-\psi/2, 2\pi+\psi/2)$. The weights may therefore be adapted for use with region 3 by offsetting $\beta$ so that the HH and HE weights for use with region 2 data are given by $w_{HH}(\beta-\psi/2,\gamma)$ and $w_{HE}(\beta-\psi/2,\gamma)$, respectively.

One potential problem with a HA scan is that the weights applied to the Radon space, as illustrated in FIG. 11, are discontinuous along the vertical lines $\gamma=-\gamma_m+\alpha$ and $\gamma=\gamma_m-\alpha$. These discontinuities in the weights can lead to streaks originating from off-center objects in the tomogram. The streaks can be eliminated by feathering or blending the halfscan weights (i.e., the weights applied to region 2 data) with the fullscan weights (i.e., the weights applied to region 3 data) and with the zero weights (i.e., the weights relating to region 1) along these two lines of discontinuity. Preferably, the feathering is performed in the regions where $-\gamma_m+\alpha<\gamma<-\gamma_m+\alpha+\zeta$ and where $\gamma_m-\alpha-\zeta<\gamma<\gamma_m-\alpha$, where $\zeta$ represents the angular extent of the feathering region. The boundaries of the feathering region are shown as vertical lines in FIG. 11 located where $\gamma=-\gamma_m+\alpha$, where $\gamma=-\gamma_m+\alpha+\zeta$, where $\gamma=\gamma_m-\alpha-\zeta$, and where $\gamma=\gamma_m-\alpha$. The feathering may be performed as discussed above in connection with the above-listed Equation (8). In one preferred embodiment, $\zeta$ is selected so that the feathering region extends over a region of about twenty detectors.

Figure 3A:
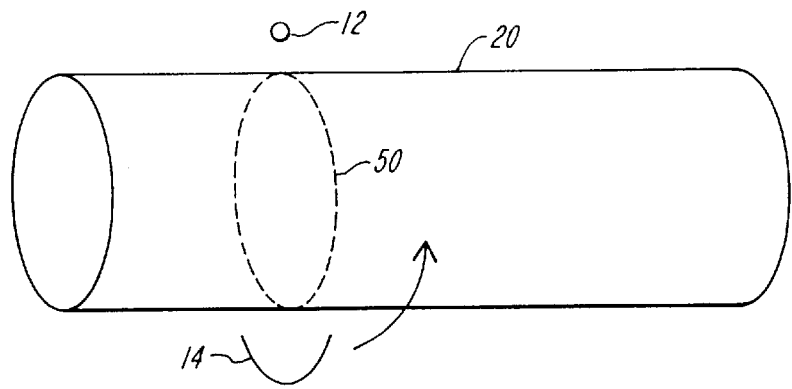
FIG. 3A illustrates an isometric view of the slice plane of data collected during a CZA scan.
Figure 3B:
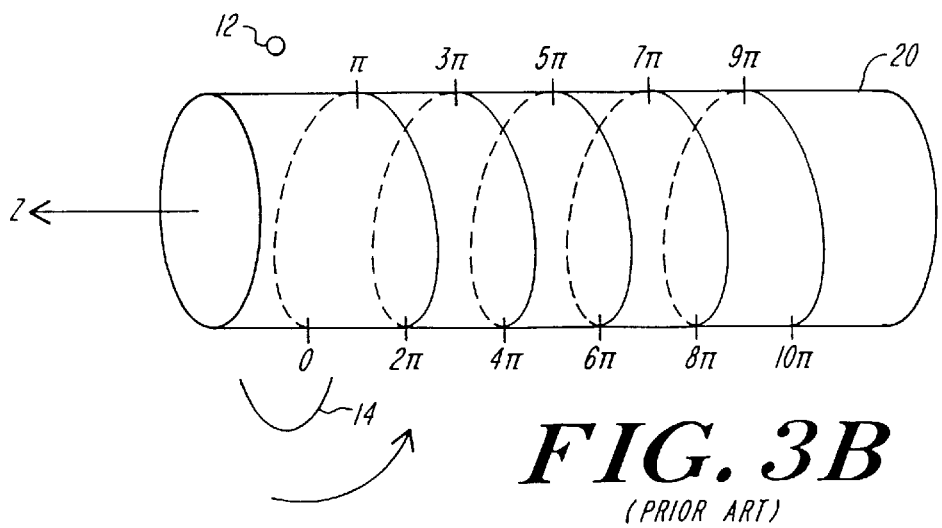
FIG. 3B illustrates an isometric view of a set of loci of the Z-axis position of every fan beam projection generated during a CSH scan for fan beam projections in the range (0,10π)
Figure 4:
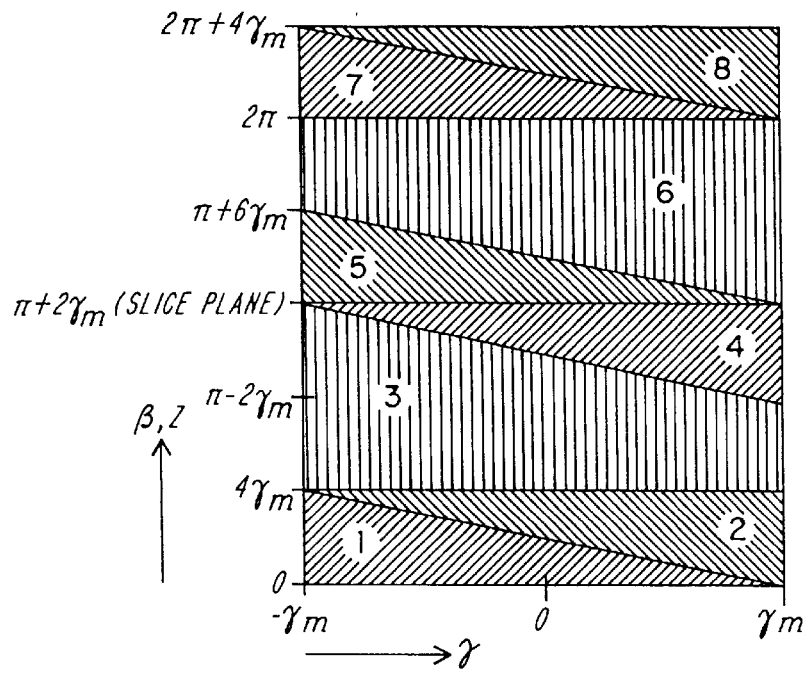
FIG. 4 is a graph of the Radon space used by a HH scan to generate a tomogram at a slice plane corresponding to a fan beam projection angle of $\pi+2\gamma_m$.
Figure 5:
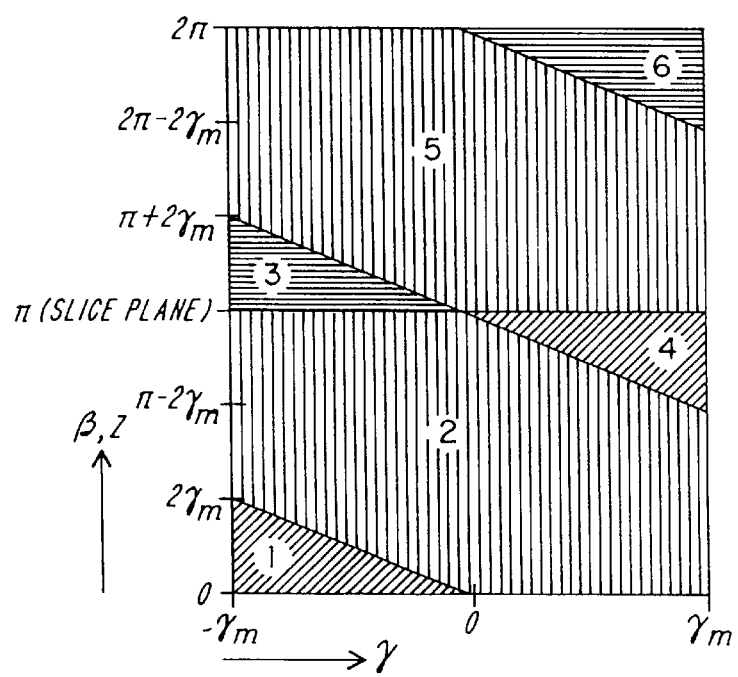
FIG. 5 is a graph of the Radon space used by a HE scan to generate a tomogram at a slice plane corresponding to a fan beam projection angle of π.
Figure 7A:
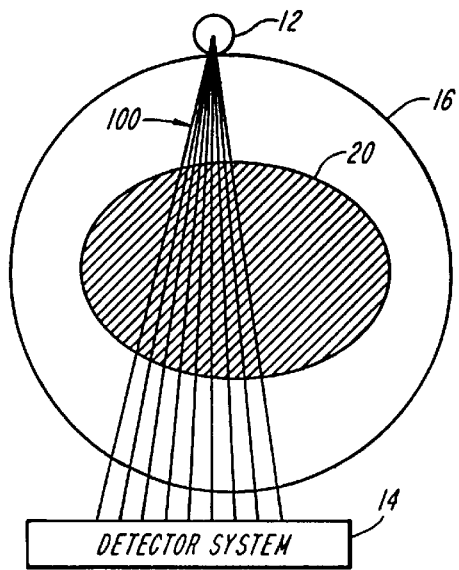
FIG. 7A is a simplified schematic axial view of a prior art CT scanner illustrating some of the rays that form a single fan beam projection.
Figure 7B:
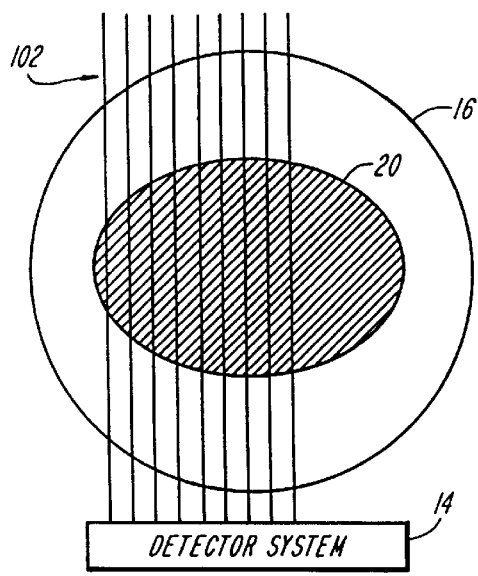
FIG. 7B is a simplified schematic axial view of a prior art CT scanner illustrating some of the rays of a single parallel beam projection.
Figure 8A:
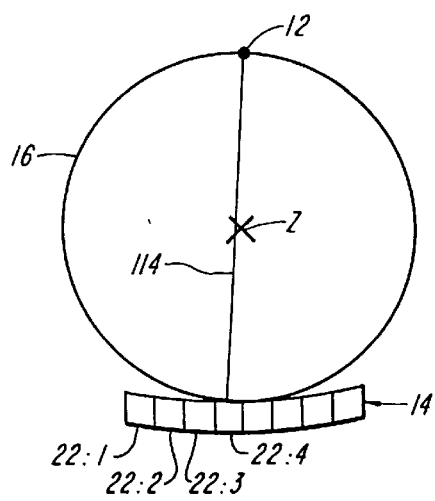
FIGS. 8A and 8B illustrate one method of rebinning fan beam projection data into reordered projection data.
Figure 8B:
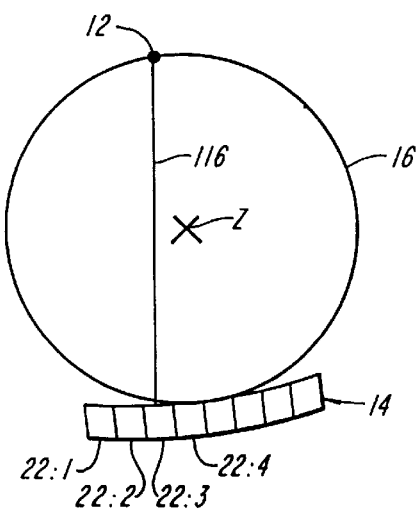

As stated above, the disk (and X-ray source and detector system) may rotate on the order of, for example, twenty complete revolutions (i.e., $40\pi$) about the patient during a single CSH scan. The data collected during this scan may be used to generate a plurality of tomograms at a corresponding plurality of slice planes. As thus far described, HA scanning requires fan beam projection data for $\beta$ in the range $(x, x+4\pi)$, where x is an arbitrary starting angle, to generate a tomogram at a slice plane corresponding to a projection angle of $x+2\pi$. Referring to FIG. 3B (which illustrates the Z-axis position corresponding to each projection angle in a helical scan for projection angles in the interval $(0,10\pi)$), as thus far described, HA scanning may be used to generate a tomogram at any slice plane (i.e., Z-axis position) corresponding to projection angles in the range $(2\pi,8\pi)$. However, as thus far described, HA scanning can not be used to generate any tomograms at slice planes corresponding to projection angles in the range $(0,2\pi)$ (i.e., at the beginning of the scan), and in the range $(8\pi,10\pi)$ (i.e., at the end of the scan).

Figure 12:
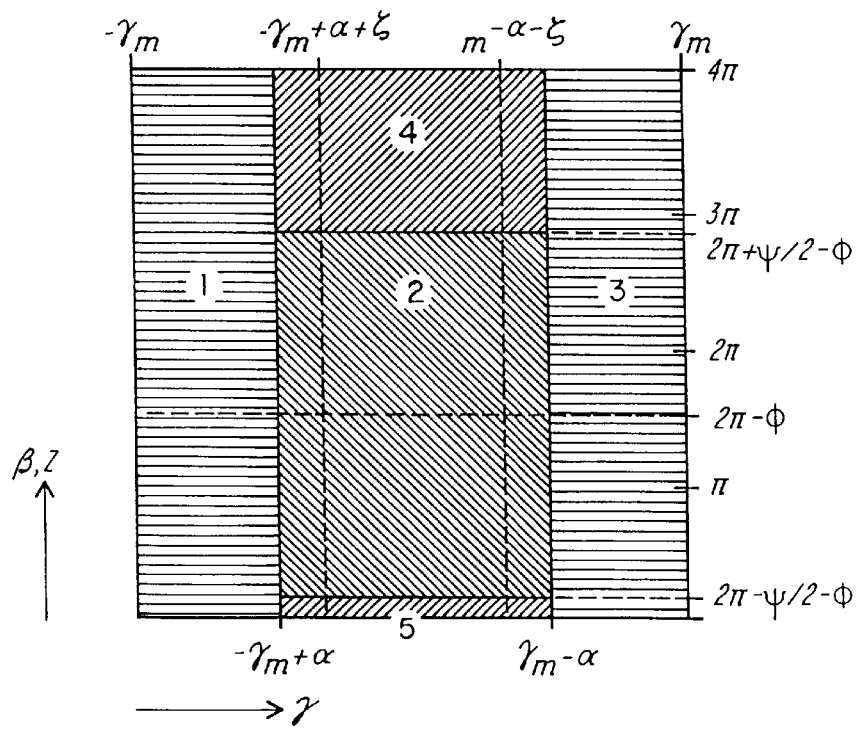
FIG. 12 is a graph of the Radon space used by HA according to the invention to generate a tomogram at a slice plane corresponding to a projection angle of $2\pi-\phi$.

Still referring to FIG. 3B, a HA scan can be modified to generate tomograms at slice planes corresponding to projection angles in the range $(\pi,2\pi)$ (i.e., at the beginning of the scan) and in the range $(8\pi,9\pi)$ (i.e., at the end of the scan). FIG. 12 illustrates a modified version of the Radon space which may be used to generate tomograms at slice planes corresponding to projection angles in the range $(\pi,2\pi)$. As compared with FIG. 11, in FIG. 12 region 2 has been shifted downward by an amount $\phi$, thus shrinking the extent of region 5 and expanding the extent of region 4. However, since region 2 still extends over a range of $\psi$ projection angles, a helical halfscan technique may be used to reconstruct a tomogram at a slice plane corresponding to a projection angle of $2\pi-\phi$ from the data in region 2. Similarly, the $4\pi$ of projection data in region 3 may also be used to contribute to that tomogram. The weights applied to regions 2 and 3 should also be offset to an amount equal to $\phi$. So, if HH or HE scanning techniques are used for the helical halfscan technique, the weights for region 2 are given by $w_{HH}(\beta-\pi-2\gamma_m+\phi,\gamma)$ or $w_{HE}(\beta-\pi+\phi,\gamma)$, respectively. Similarly, if a HI scanning technique is used for the helical fullscan technique, the weights for region 3 are given by the following Equation (10).

$$w_{HI}(\beta,\gamma) = \begin{cases} \dfrac{\beta + \phi}{2\pi} & \beta \leq 2\pi \\ \dfrac{4\pi - \beta - \phi}{2\pi} & \text{elsewhere} \end{cases} \quad (10)$$

Selecting $\phi$ equal to $\pi$ permits reconstruction of a tomogram at a slice plane corresponding to a projection angle of $\pi$. So this procedure may be used at the beginning of the scan to generate tomograms at slice planes corresponding to projection angles in the interval $(\pi,2\pi)$. Those skilled in the art will appreciate that a similar procedure (involving raising region 2 of the Radon space rather than lowering it) may be used to generate tomograms at the end of a scan.

Figure 13A:
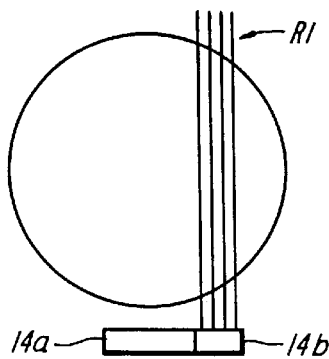
FIG. 13A illustrates a simplified schematic view of a portion of a projection collected by an asymmetric portion of a detector system.
Figure 13B:
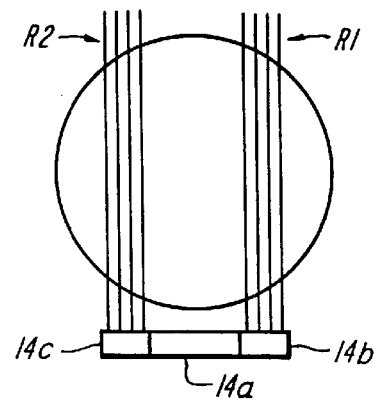
FIG. 13B illustrates a simplified schematic view of portions of a projection collected by an asymmetric portion of a detector system as well as a portion of a projection that could be collected by a missing portion of a detector system if such missing portion were present.

Thus far, the invention has been discussed in connection with filtered backprojection algorithms that generate tomograms from fan beam projection data. While a HA scan has been discussed in connection with fan beam CT systems, those skilled in the art will appreciate that HA scanning may also be used with parallel beam CT systems. The operation of a HA scan may be intuitively understood in terms of a parallel beam reconstruction algorithm. The data in region 2 of FIG. 11 may be rebinned and interleaved to generate CZA parallel beam projections $P_p(\beta,\gamma)$ for $\beta$ in the range $(0,\pi)$ and the data in region 3 of FIG. 11 may be rebinned and interleaved to generate CZA parallel beam projections $P_p(\beta,\gamma)$ for $\beta$ in the range $(0,2\pi)$. Initially it may appear that a factor of two is missing from one of the two sets of weights. However, fan beam data are not collected for region 1 and the doubled set of data in region 3 are used to compensate for the missing data in region 1. FIGS. 13A and 13B illustrate this relationship.

FIG. 13A shows the ray paths R1 for the portion of a parallel beam projection that is measured by the asymmetric portion 14b of detector system 14. In addition to the ray paths R1, FIG. 13B shows the rays paths R2 for the portion of a parallel beam projection that could have been measured by the missing portion 14c of the detector system if such a missing portion were present. As those skilled in the art will appreciate, in the absence of patient translation motion, the data collected by the asymmetric portion 14b for parallel beam projection angles in the range $(0,2\pi)$ is equivalent to the data that would be collected by detector portions 14b, 14c for parallel beam projection angles in the range $(0,\pi)$. So the extra $\pi$ of projection data collected for the asymmetric portion 14b compensates for the data that is not collected by the missing portion 14c.

When HA scanning is used in connection with a parallel beam filtered back projection algorithm, the weights may be applied to the Radon space (as illustrated in FIG. 11) before or after rebinning and/or interleaving. When the weights are applied prior to rebinning, the weights are preferably feathered between regions 2 and 4 near the horizontal line where $\beta$ equals $2\pi+\psi/2$ and between regions 2 and 5 near the horizontal line where $\beta$ equals $2\pi-\psi/2$. This feathering is analogous to the well known overscan procedures used in CZA scanning. Overscan compensates for patient translation motion that occurs during a CZA scan and causes the projection data at the starting projection angle to be different than the projection data at the finishing angle (e.g., where the finishing angle equals the starting angle plus $2\pi$). Overscan is described, for example, in detail in D. L. Parker, V. Smith, and J. H. Stanley, *Dose minimization in computed tomography overscanning*, Medical Physics, Vol. 8, 706–711 (1981).

Figure 14:
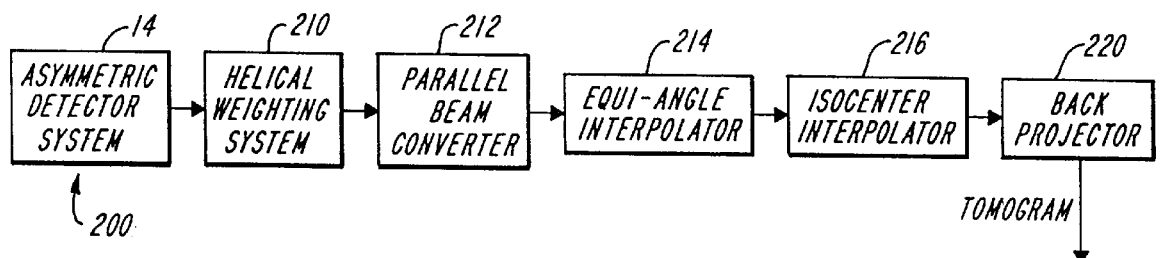
FIG. 14 shows a block diagram of a portion of one preferred CT scanner constructed according to the invention for use with asymmetric detector systems.

FIG. 14 shows a block diagram of a portion of one preferred CT scanner 200 constructed according to the invention for generating tomograms from CSH scan data. Scanner 200 includes asymmetric detector system 14, a helical weighting system 210, a parallel beam converter 212, a prior art equi-angle interpolator 214, a prior art isocenter interpolator 216, and a back projector 220. Asymmetric detector system 14 collects the fan beam projection data and applies it to helical weighting system 210. The latter applies the feathered weights for the HA scan to the fan beam projection data as has been discussed above in connection with FIGS. 11 and 12. The weighted projection data is then applied to parallel beam converter 212 which reorders and interleaves the fan beam projection data to generate parallel beam projection data. Equi-angle interpolator 214 receives the parallel beam projections and generates therefrom equi-angle projections by filling in the undefined data points in the exterior regions of the parallel beam projections. Isocenter interpolator 216 receives the equi-angle projections and generates therefrom isocenter projections. Back projector 220 receives the isocenter projections and generates a tomogram from this data using a parallel beam reconstruction algorithm. In an alternative embodiment of scanner 200, parallel beam converter 212, equi-angle interpolator 214, and isocenter interpolator 216 are eliminated, and back projector 214 generates tomograms using a fan beam reconstruction algorithm.

Since scanner 200 includes an asymmetric detector system, every parallel beam projection generated by converter 212 includes a central region and two exterior regions. Further, as previously described, every other data point in the exterior regions is undefined. Equi-angle interpolator 214 generates the equi-angle projections from the parallel beam projections by replacing every undefined data point in the parallel beam projections with an interpolated point. As is known in the prior art, interpolator 214 may generate these interpolated data points according to weighted averages of neighboring data points. For example, interpolator 214 may generate a value for an undefined data point $D:i$ according to a weighted average of defined adjacent data points $D:i-1$ and $D:i+1$. By replacing the undefined data points with interpolated data points, interpolator 214 insures that the angular spacing between all adjacent data points in the equi-angle projections are equal.

Figure 15:
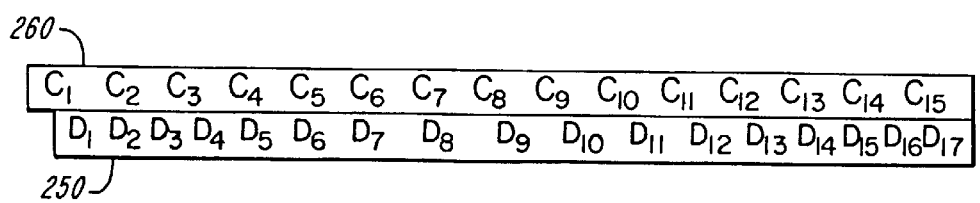
FIG. 15 shows the uneven linear spacing in a parallel beam projection and the even spacing in projection generated by an isocenter interpolator.

Isocenter interpolator 216 generates the isocenter projections from the equi-angle projections so that the linear distance between all adjacent data points in the isocenter projections are all equal. FIG. 15 shows an equi-angle projection 250 including data points $D:i$, for all i from one to seventeen. Since projection 250 is an equi-angle projection, all the data points $D:i$ are defined. Most equi-angle projections include hundreds of data points, however, for convenience of illustration, the seventeen data point projection 250 will now be discussed. FIG. 15 illustrates the linear spacing between each data point $D:i$ (i.e., the linear spacing between the rays used to generate the data points) in projection 250. As shown, the spacing between data points near the center of the projection 250 is much greater than the spacing between the data points near the ends of the projection. This uneven spacing is a well known consequence of converting fan beam projections to parallel beam projections. Isocenter interpolator 216 generates an isocenter projection 260 of data points $C:i$ from the equi-angle projection 250. As shown, all the data points in projection 260 are equally spaced apart from one another. As is known in the prior art, isocenter interpolator 216 may generate each data point $C:i$ according to a weighted average of a neighborhood of data points in projection 250 according to the following Equation (11).

$$C:i = \sum_{j=-x/2}^{x/2} b:j * D:j \qquad (11)$$

Figure 16:
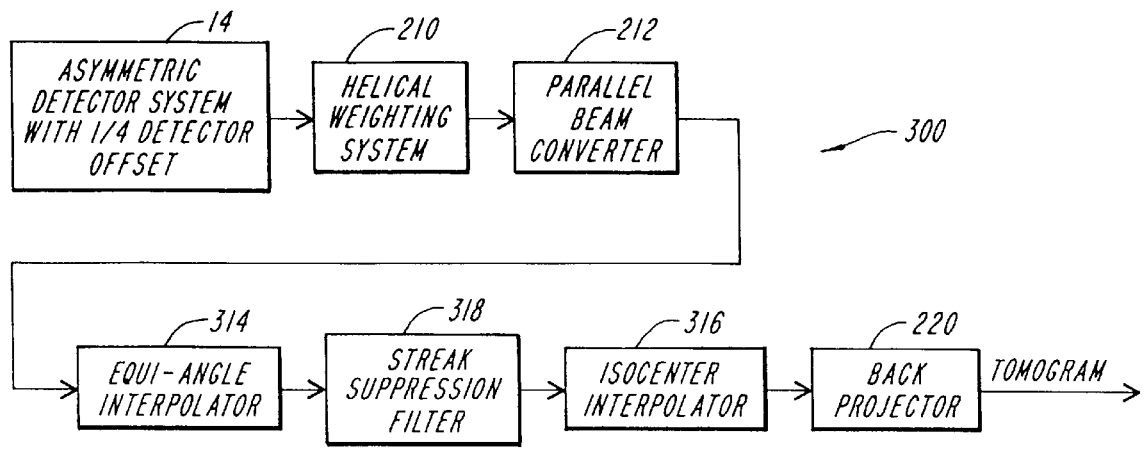
FIG. 16 shows a block diagram of a portion of another preferred CT scanner constructed according to the invention for use with asymmetric detector systems having a quarter detector offset.

Back projector 220 then generates a tomogram from the isocenter projections. The operation of helical weighting system 210 permits scanner 200 to generate improved tomograms. Scanner 200 functions well when asymmetric detector system 14 does not use a detector offset (e.g., quarter detector offset). However, the invention also provides methods of and apparatus for generating tomograms from CSH scan data collected with asymmetric detector systems that do use a detector offset. FIG. 16 shows a block diagram of a preferred scanner 300 constructed according to the invention for generating tomograms from CSH scan data collected with an asymmetric detector system that includes a quarter detector offset. Improved scanner 300 includes asymmetric offset detector system 14, helical weighting system 210, parallel beam converter 212, an improved helical equi-angle interpolator 314, an improved helical streak suppression filter 318, an improved helical isocenter interpolator 316, and back projector 220.

In scanner 300, the asymmetric offset detector system 14 collects fan beam projection data and applies this data to helical weighting system 210. The latter applies the feathered weights for HA to the fan beam data and then applies the weighted fan beam projection data to parallel beam converter 212. Converter 212 reorders and interleaves the fan beam data to generate parallel beam projections, each of which is characterized by a central region and two exterior regions. Improved equi-angle interpolator 316 generates equi-angle projections by doubling the value of all data points in the exterior regions and by replacing all undefined data points with data points having a value of zero. The equi-angle projections generated by interpolator 314 are applied to streak suppression filter 318 which suppresses high amplitude, high spatial frequency components in the projection data so as to suppress streaks in the resulting tomograms. The filtered projections generated by streak suppression filter 318 are applied to improved isocenter interpolator 316 which generates isocenter projections. Back projector 214 receives the isocenter projections generated by isocenter interpolator 316 and generates tomograms from this data.

In scanner 300, the parallel beam projections generated by converter 212 are applied to improved helical equi-angle interpolator 314. In the prior art, equi-angle interpolation is normally performed by interpolating a new data point between every pair of adjacent data points in each of the exterior regions. However, rather than perform the prior art equi-angle interpolation, improved equi-angle interpolator 314 replaces the undefined data points with data points that have a value of zero and doubles the value of all the data points in the exterior regions. Prior art methods of equi-angle interpolation essentially use the even data points in one exterior region to generate an interpolated set of odd data points for that region, and also use the odd data points in the other exterior region to generate an interpolated set of even data points for that region. Further, the operations performed by improved equi-angle interpolator 314 are simpler (i.e. less computationally intensive) than those performed by interpolator 214.

Streak suppression filter 318 receives the equi-angle projections generated by equi-angle interpolator 314 and generates therefrom streak corrected projections which are in turn applied to isocenter interpolator 316. Streak suppression filter 318 suppresses high amplitude, high spatial frequency components from the projections so as to reduce streak artifacts in the resulting tomograms. A version of streak suppression filter 318 that is useful for CZA scanning is described in U.S. patent application Ser. No. 08/587,468, filed Jan. 17, 1996 and entitled STREAK SUPPRESSION FILTER FOR USE WITH COMPUTED TOMOGRAPHY SYSTEM (Attorney Docket No. ANA-081), which is hereby incorporated by reference.

Figure 17:
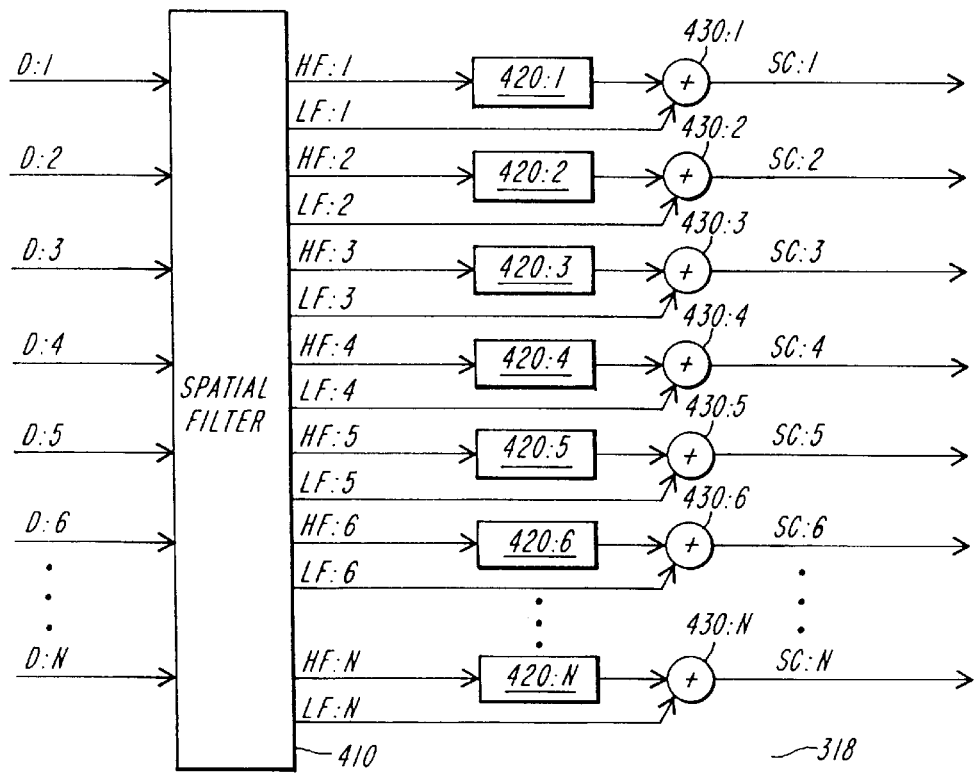
FIG. 17 shows a block diagram of a streak artifact suppression filter constructed according to the invention for use with CSH scanning.

FIG. 17 shows a block diagram of streak suppression filter 318 constructed according to the invention. Filter 318 receives the projections generated by equi-angle interpolator 316. Each of these projections include N data points D:1 through D:N. From these data points, streak suppression filter 318 generates a set of streak corrected data points SC:1 through SC:N and these data points are applied to isocenter interpolator 316. Filter 318 includes a spatial filter 410, a set of N threshold devices 420: 1 through 420:N, and a set of N adders 430:1 through 430:N. The spatial filter 410 receives all the data points D:i, for all i from one to N. For every data point D:i the spatial filter generates a high frequency data point HF:i and a low frequency data point LF:i. The high and low frequency data points HF:i and LF:i are representative of the spatial high and spatial low frequency content, respectively, of a neighborhood of data points D:i−x/2 to D:i+x/2 around the data point D:i, where x defines the size of the neighborhood. Each high frequency data point HF:i is applied to a corresponding threshold device 420:i, for all i from one to N. The threshold device 420:i generates a clipped data point and applies this data point to one input terminal of the adder 430:i, for all i from one to N. The low frequency data point LF:i is applied to the other input terminal of the adder 430:i, for all i from one to N. The adder 430:i adds the data points present at its two input terminals to generate the streak corrected data point SC:i, for all i from one to N.

Spatial filter 410 normally generates the low frequency data point LF:i by applying a low-pass filter to the neighborhood of data points around the data point D:i, and normally generates the high frequency data point HF:i by subtracting the low frequency data point LF:i from the data point D:i. When the high and low frequency data points are generated in this manner, the data point D:i may be exactly recovered by summing the high and low frequency data points HF:i and LF:i.

The threshold devices 420:i generate the clipped data points by thresholding the high frequency data points, or by compressing the high frequency data points, so as to reduce high amplitude, high spatial frequency portions of the streak corrected projections. When the high frequency data point HF:i is of a relatively low amplitude, the threshold device 420:i generates its clipped data point so that it is exactly equal to the high frequency data point HF:i. In this case, adder 430:i generates a streak corrected data point SC:i that is identical to the original data point D:i (because the adder 430:i sums the low frequency data point LF:i and the clipped data point generated by the threshold device 420:i, and this clipped data point is equal to the high frequency data point HF:i). However, when the high frequency data point HF:i is of a relatively large amplitude, the threshold device 420:i generates its clipped data point so that its amplitude is lower than that of the high frequency data point HF:i. In this case, the adder 430:i generates the streak corrected data point SC:i so that it is not identical to the data point D:i. Rather, the high amplitude, high spatial frequency components in the neighborhood of data points around the data point D:i are suppressed to generate the streak corrected data point SC:i. So in general, the streak suppression filter suppresses high amplitude, high frequency components.

The above-referenced U.S. patent application Ser. No. 08/587,468, essentially describes the spatial filter 410 as generating the low frequency data point LF:i as a weighted average of the neighborhood of data points around the data point D:i according to the following Equation (12).

$$LF{:}i = \sum_{j=-x/2}^{x/2} a{:}j * D{:}(i-j) \quad (12)$$

Streak suppression filter 318, when using Equation (12), works well for suppressing streaks in CZA scan data. However, when filter 318 operates in this fashion, it tends to introduce unwanted artifacts into tomograms generated from CSH scan data. As stated above, there tends to be a discrepancy between odd data points and even data points in any single parallel beam projection generated during a helical scan, and this discrepancy appears as high frequency noise. As a result of this high frequency noise, when streak suppression filter 318 operates as discussed above, virtually every high frequency data point is above threshold and is compressed by the threshold devices 420:i. However, this compression is introduced as a result of the patient motion occurring during a helical scan rather than as a result of high contrast (streak artifact generating) features in the patient.

In the preferred embodiment of improved helical streak suppression filter 318, spatial filter 410 generates odd low and high frequency data points LF:2i+1 and HF:2i+1, respectively, using only odd data points, and generates even low and high frequency data points LF:2i and HF:2i, respectively, using only even data points. For example, spatial filter 410 may generate the low frequency data points LF:i according to the following Equation (13).

$$LF{:}i = \sum_{j=-x/2}^{x/2} a{:}j * D{:}i - 2j \quad (13)$$

In this fashion, improved helical streak suppression filter 318 avoids combining data from even and odd data points in a single projection and thereby prevents the patient motion inherent in any helical scan from corrupting the operation of the filter 318. When streak suppression filter 318 operates in this fashion, it responds to streak producing structures in the patient (i.e., high contrast features) rather than to patient motion, and therefore tends to reduce artifacts in the resulting tomograms generated from CSH scan data. The streak corrected data points generated by filter 318 are then applied to improved helical isocenter interpolator 316 (shown in FIG. 16). Isocenter interpolator 316 generates isocenter projections from the streak corrected projections. As illustrated in FIG. 15, each of the isocenter projections 260 generated by interpolator 316 includes a set of data points $C_i$. However, improved isocenter interpolator 316 does not generate the data points $_i$ C according to the above Equation (11) as does interpolator 216. Rather, interpolator 316 generates the data points $C_i$ according to the following Equation (14).

$$C{:}i = \sum_{j=-x/2}^{x/2} b{:}j * D{:}i - 2j \quad (14)$$

Basically, Equation (11) is unsatisfactory because it generates each data point C:i as a weighted average of odd and even data points. As was stated above, combining information from odd and even data points in this fashion tends to introduce artifacts into the tomograms. Therefore, improved isocenter interpolator 316 preferably generates each data point C:i as a weighted average of a neighborhood of odd data points, or as a weighted average of a neighborhood of even data points according to the above Equation (14). This form of isocenter interpolation reduces artifacts in the resulting tomograms generated by CSH scanning. In one preferred embodiment, the weights b:i are selected so that the data points C:i are generated according to a six point Lagrange interpolation (otherwise known as Everett interpolation). Six point Lagrange interpolation is discussed in detail in, for example, *Handbook of Mathematical Functions*, edited by M. Abramowitz and I. A. Stegun, Dover Publications, New York (1970).

While scanner 300 (shown in FIG. 16) is a preferred embodiment of the invention, those skilled in the art will appreciate that many variations of scanner 300 are also embraced within the invention. For example, many other types of filters and devices are normally included in a CT scanner. By way of example, the scanner would normally include a DAS disposed between the detector system and the helical weighting system. Many other types of filters may also be included, such as filters that perform temperature compensation, or afterglow compensation. Also, while the preferred scanner includes the helical weighting system 210 that applies the HA scan weights to the projection data, other types of weighting systems, such as prior art weighting systems, may be used and the equi-angle interpolator 314, streak suppression filter 318, and isocenter interpolator 316 may each be used to improve the quality of the resulting tomograms. Also, while detector systems with a quarter detector offset have been primarily discussed, those skilled in the art that the invention may readily be adapted for use with detector systems characterized by other types of offsets. Further, while the invention has been discussed in connection with CSH scanning, those skilled in the art will appreciate that the invention may be easily adapted for use with non-constant speed helical scanning.

Halfscan reconstructed images are typically obtained by reconstructing a minimally complete set of fan beam projection data, i.e., fan beam projection data obtained at projection angles over a range of $\pi$ radians plus the fan angle. The problem of reconstructing halfscan data acquired with an asymmetric detector array is similar to that encountered in helical reconstruction. Due to missing data and the weights functions applied to the data, the interleaved data are modulated between every other detector. Use of the modified destreaking and isocenter interpolation developed for helical asymmetric are an effective means of dealing with this modulation. Alternative approaches to dealing with this modulation problem, such as interpolating missing data samples, could be employed.

Two halfscan reconstruction techniques using an asymmetric detector array and acquiring data using constant Z-axis (CZA) scanning will now be described in detail. Both techniques are suitable for use with an asymmetric detector array and quarter detector offset. The first approach, referred to herein as halfscan oversize (HSO), performs a halfscan reconstruction of a halfscan acquired data set acquired at projection angles of $\pi$ radians plus the symmetric fan angle. It is used to reconstruct image data for an oversized subject, i.e., a subject which extends beyond the symmetric field of view of the scanner. The subject is assumed to be positioned within the symmetric portion of the detector array. Artifacts produced by anatomy outside the symmetric portion of the detector array are compensated by ramping the projections outside the symmetric portion of the array to zero.

In the HSO approach, the reconstruction field of view is restricted to the radius of the symmetric portion of the detector array. Outside of this radius, correction is made to compensate for artifacts introduced by anatomy outside the asymmetric portion of the array. When a patient exceeds the maximum image area, that is the physical field of view of the gantry, the projection profiles do not drop down to the baseline near the end of the detector array at certain view angles. If these data are not corrected, there will be artifacts in the reconstructed image near the area where the object exceeds the maximum field of view.

In one embodiment, a first-order correction on the projection data is used to reduce the artifacts to a satisfactory level. For example, in one particular embodiment, isocenter interpolation generates 884 data points of equal spacing from them. These 884 values are placed into a 1024-point data array, from points 71 through 954. At both ends of the data array, that is, points 1 through 70 and points 955 through 1024, data are filled with zeros for convolution.

The first-order correction is to replace the 218-point leading and trailing edges of the data array with a ramp and a reverse ramp function, respectively, such that the data value always decreases to zero gradually toward both ends of the data array.

Figure 18:
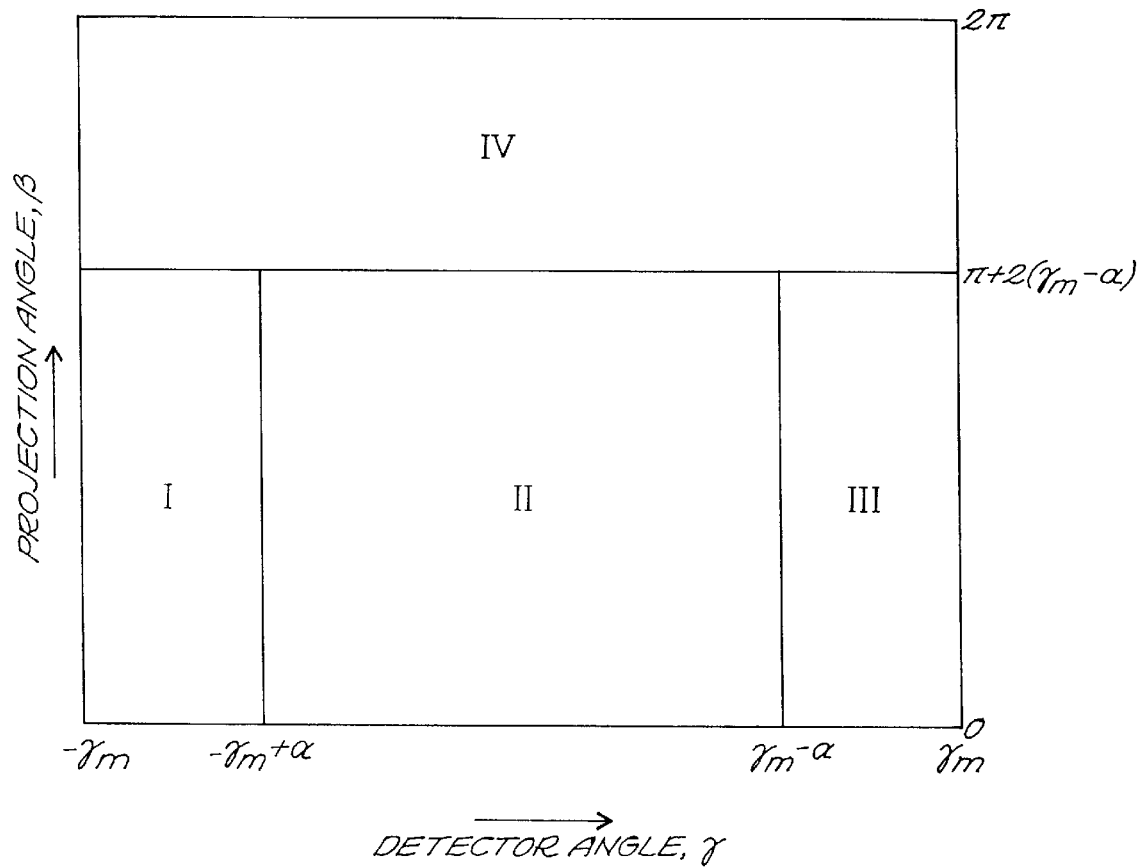
FIG. 18 is a graph of the Radon space used by the halfscan oversize (HSO) reconstruction of the present invention.

The input to the halfscan reconstruction is fan beam data collected over $\pi$ radians plus the symmetric fan angle. FIG. 18 illustrates the Radon space for the HSO reconstruction approach. The data in region I are collected using the asymmetric portion of the detector array. The data in region II are collected using the symmetric portion of the detector array. The data in regions III and IV are not collected, due to the asymmetric detector array and the halfscan acquisition, respectively, and are assumed to be zero. $\gamma_m$ is the half fan angle subtended by the asymmetric portion of the array and $(\gamma_m - \alpha)$ is the half fan angle subtended by the symmetric portion of the array. As illustrated in FIG. 18, it is assumed that $\pi + 2 (\gamma_m - \alpha)$ views of corrected data are placed in a buffer large enough to store the $2\pi$ views that are collected in a fullscan acquisition (data that is not collected is assumed to be zero).

The first step in the reconstruction procedure includes applying weights to the fan beam data. Following this, the weighted data can be input into the helical rebinning procedure, which employs modified destreaking and isocenter interpolation algorithms as described above. The data can then be passed to convolution, where a modified convolution kernel can be used to low-pass filter the interleaved projections. Backprojection and postprocessing of the image data can be performed in the same manner as fullscan reconstruction.

The fan beam data are weighted to compensate for missing data and to blend single and double sampled regions. The weights are designed such that the sum of any two weights corresponding to the same line integral are equal to one. By choosing a weighting function that is continuous and has continuous first derivatives within the symmetric portion of the detector array, the transitions between the regions are smoothed, reducing the potential for artifacts.

The value of the weighting function depends on the view and detector angles. The halfscan weighting function is defined for all view angles $\beta$ ($0 \leq \beta \leq 2\pi$) as $$w_{hs}(\beta,\gamma) = \begin{cases} f[x_{hs}(\beta,\gamma)] & -\gamma_m + \alpha \leq \gamma \leq \gamma_m - \alpha \\ 0 & \text{otherwise} \end{cases} \quad (15)$$

where the feathering function f(x) is given by $$f(x)=3x^2-2x^3. \quad (16)$$

The value of $x_{hs}$ is defined as follows:

$$x_{hs}(\beta,\gamma) = \begin{cases} \beta/2(\gamma_m - \alpha - \gamma), & 0 \leq \beta < 2(\gamma_m - \alpha - \gamma) \\ 1, & 2(\gamma_m - \alpha - \gamma) \leq \beta < \pi - 2\gamma \\ (2(\gamma_m - \alpha) + \pi - \beta)/(2(\gamma_m - \alpha) + 2\gamma), & \pi - 2\gamma \leq \beta \leq \pi + 2(\gamma_m - \alpha) \\ 0 & \pi + 2(\gamma_m - \alpha) < \beta \leq 2\pi \end{cases} \quad (17)$$

Note that the weighting function is fixed by the scan geometry and can be stored in a lookup table.

The weighted halfscan data can be input into the helical rebinning procedure described above. The input to the rebinning procedure is $2\pi$ of fan beam data. The output of the rebinning process is a set of interleaved parallel projections suitable for input to the convolution stage of the reconstruction. A summary of the rebinning process is presented below.

Parallel views can be interpolated from the fan beam projections using the same method as described previously for helical reconstruction. The interpolation procedure used to determine missing data samples in the asymmetric regions is not performed. The destreaking algorithm used in fullscan reconstruction can be modified to be the same as that used in helical reconstruction described above. The projection data can be interleaved in the same manner as a fullscan acquisition. Zeros are interleaved in the data where data is missing (i.e., views in the angular range $\pi+2(\gamma_m-\alpha)<\beta\leq2\pi$ that are not collected). Isocenter interpolation produces equally spaced parallel samples with a spacing equal to half the detector spacing at isocenter. As in helical reconstruction, isocenter interpolation is performed using samples spaced two samples apart.

Compensation is required for subjects that extend beyond the symmetric portion of the field of view. A correction can be performed by ramping the last samples at the boundary of the symmetric region to zero at the edges of the interleaved data set. Convolution is generally performed using kernels modified to go to zero at half the scanner's sampling rate. Sharper kernels can also be used to produce images with slightly more resolution, at the expense of increased aliasing artifacts. Halfscan images can be produced by backprojection in the same manner as fullscan data. Due to the magnitude of the weighting function applied to the data, the output image must be multiplied by a factor of two.

The second approach, referred to herein as halfscan asymmetric (HSA), is intended for halfscan reconstruction of fullscan data and dynamic scan data. The algorithm reconstructs the central or symmetric portion of the detector array using halfscan reconstruction and the asymmetric region using fullscan reconstruction. That is, in the symmetric portion of the array, projection angles for $\pi$ radians plus the symmetric fan angle are used, and in the asymmetric portion, $2\pi$ radians of data are used.

Figure 19:
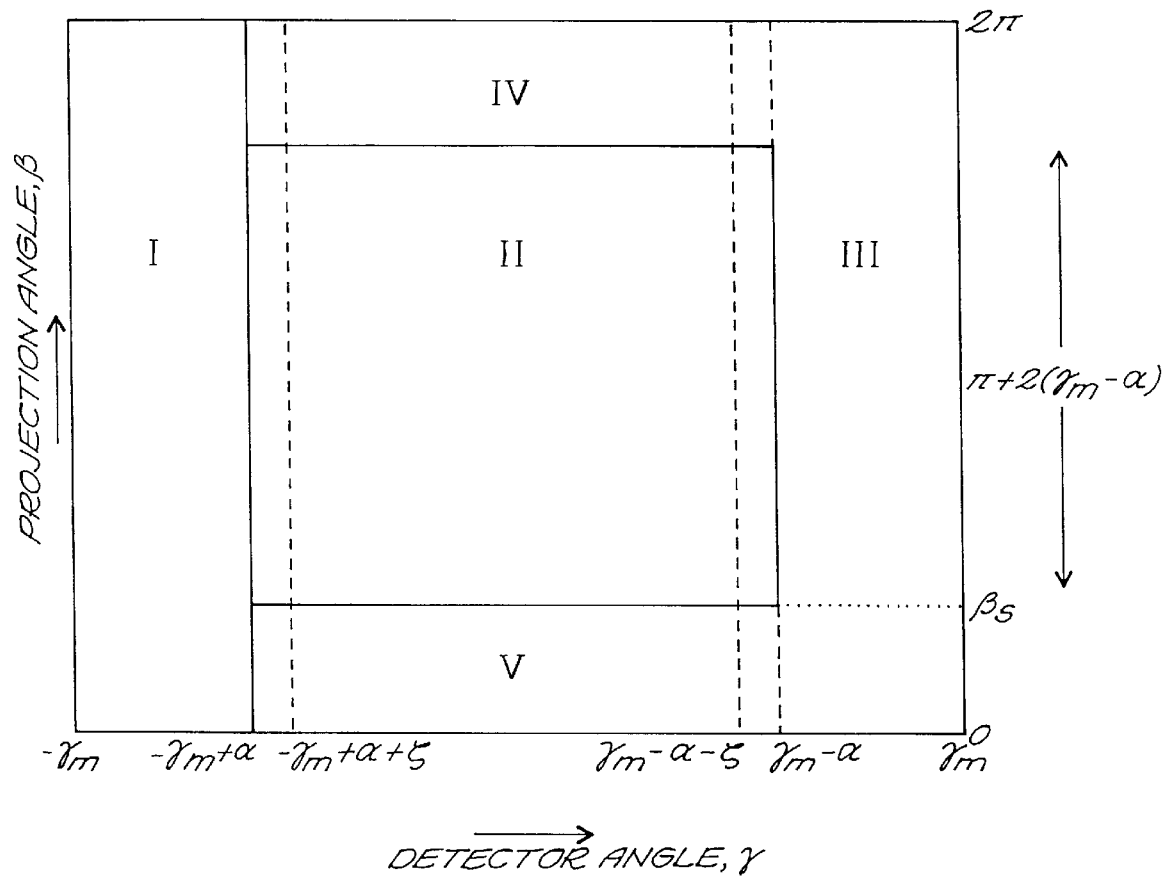
FIG. 19 is a graph of the Radon space used by the halfscan asymmetrical (HSA) reconstruction of the present invention.

The input to the HSA reconstruction is fan beam data collected over $2\pi$ radians. FIG. 19 illustrates the Radon space for the HSA approach. Region I corresponds to the asymmetric portion of the detector array. The data in regions II, IV and V are collected using the symmetric portion of the detector array. Due to the application of the halfscan weights in the symmetric portion of the array, regions IV and V are zeroed. The data in region III are not collected, due to the asymmetric detector array and are assumed to be zero. $\gamma_m$ is the half fan angle subtended by the asymmetric part of the array, $\gamma_m-\alpha$ is the half fan angle subtended by the symmetric portion of the array and $\zeta$ is the angle subtended by the feathered region. The angle $\beta_s$ is the view angle corresponding to the start of the halfscan weighted region weights. As illustrated by FIG. 19, the technique employs a fullscan reconstruction in the asymmetric portion of the detector array and halfscan reconstruction in the central portion. Discontinuities between the two regions are smoothed using a feathering function.

The reconstruction procedure includes applying the HSA weights to the fan beam data. In dynamic reconstructions, a set of views spanning $2\pi$ radians is extracted from a multiple rotation data set and a set of weights is applied with the halfscan region centered on the data buffer. For HSA reconstruction of fullscan data, views spanning $2\pi$ are also available. In this case, the position of the halfscan region is allowed to move in the view direction, to allow halfscan reconstruction of different data segments.

Following this procedure, the weighted views can be input into the helical rebinning procedure, which employ modified destreaking and isocenter interpolation algorithms as described above. The data can then be passed to convolution, where a modified convolution kernel can be used to low-pass filter the interleaved projections. Backprojection and postprocessing of the image data can be performed in the same manner as fullscan reconstruction.

The HSA weighting function $w_{hsa}(\beta,\gamma)$ can be defined in terms of the halfscan weighting function $w_{hs}(\beta,\gamma)$, given by Equations (15)–(17) and the fullscan weighting function $w_{fs}(\gamma)$. The fullscan weighting function is given by $$w_{fs}(\gamma) = \begin{cases} 1, & \gamma < 0 \\ 0, & \gamma \geq 0 \end{cases} \quad (18)$$

Discontinuities between the symmetric and asymmetric portion of the array are smoothed by feathering the halfscan and fullscan weighting functions. The feathering weighting function $W_f(\gamma)$ is independent of view angle and is given by $$w_f(\gamma) = \quad (19)$$

$$\begin{cases} 1, & -\gamma_m \leq \gamma < -\gamma_m + \alpha \\ f\left(-\dfrac{\gamma+\gamma_m-\alpha-\zeta}{\zeta}\right), & -\gamma_m + \alpha \leq \gamma < -\gamma_m + \alpha + \zeta \\ 0, & -\gamma_m + \alpha + \zeta \leq \gamma < \gamma_m - \alpha - \zeta \\ f\left(\dfrac{\gamma-\gamma_m+\alpha+\zeta}{\zeta}\right), & \gamma_m - \alpha - \zeta \leq \gamma \leq \gamma_m - \alpha \end{cases}$$

where $\alpha$ is the angular width of the feathering region and the feathering function $$f(x)=3x^2-2x^3. \quad (20)$$

The final HSA weights are generated with $$w_{hsa}(\beta,\gamma)=w_f(\gamma)w_{fs}(\gamma)+[1-w_f(\gamma)]w_{hs}(\beta-\beta_s,\gamma), \quad (21)$$

where $\beta_s$ determines the starting angle of the halfscan region relative to the fullscan region.

In HSA reconstructions of dynamic scan data, the $2\pi$ views extracted from the multiple rotation data set are weighted such that the halfscan region is centered in the view direction. This requirement is satisfied by setting $$\beta_s = \frac{1}{2}\pi - \gamma_m + \alpha. \tag{22}$$

In HSA reconstruction of fullscan data, the halfscan region is allowed to vary over the data set (i.e., $0 \leq \beta_s \leq \pi - 2\gamma_s$), depending on the portion of the data that is to be reconstructed.

The weighted halfscan data can be input into the helical rebinning procedure as described above. The procedure can be modified to make it suitable for reconstruction of halfscan data.

The projection data can be interleaved in the same manner as a fullscan acquisition. The interpolation procedure used to determine missing data samples in the asymmetric regions can be performed using the helical equiangle interpolation procedure. The isocenter interpolation procedure can also be the same as that used in HSO reconstruction. Regarding oversized subject correction, compensation for subjects that extend beyond the asymmetric portion of the field of view can be performed by extending the projection data beyond the asymmetric portion of the array using ramp functions which decrease to zero in the same manner as in fullscan reconstruction. The convolution backprojection and post-processing procedures can be the same as those used in HSO. Also, as with HSO reconstruction, the output image must be multiplied by a factor of two.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A method of generating tomographic image data for an object, said method comprising:

providing a radiation source for directing radiation through the object;

providing an array of detectors for receiving the radiation from the object to acquire fan beam projection data used to generate the image data for the object, the array of detectors and the radiation source being rotatable about a center of rotation in the object through a plurality of projection angles to acquire the fan beam projection data, the ends of the array of detectors defining a fan angle having an apex defined by the radiation source, a line connecting the radiation source and the center of rotation dividing the fan angle into a first partial fan angle and a second partial fan angle, the first and second partial fan angles being unequal, wherein each line connecting each detector in the array of detectors and the radiation source defines a detector angle $\phi$ with the line connecting the radiation source and the center of rotation, the smaller of the first and second partial fan angles being $\phi_{MIN}$ and the larger of the first and second partial fan angles being $\phi_{MAX}$; and generating the slice of image data using a subset of a complete set of fan beam projection data for the slice, wherein the complete set of fan beam projection data for the slice comprises all of the fan beam projection data available from a complete revolution of the radiation source and the array of detectors about the center of rotation.

2. The method of claim 1 wherein at least a portion of the object lies outside a field of view of the array of detectors.

3. The method of claim 1 wherein the slice of image data is generated from fan beam projection data acquired by a subset of the detectors in the array of detectors.

4. The method of claim 1 wherein the slice of image data is generated from fan beam projection data acquired at fewer than all of the fan beam projection angles for a complete revolution of the radiation source and the array of detectors about the center of rotation.

5. The method of claim 1 further comprising weighting the fan beam projection data prior to generating the slice of image data.

6. The method of claim 5 further comprising using a first weighting scheme to weight data acquired by detectors with $|\phi| < \phi_{MIN}$ and using a second weighting scheme to weight data acquired by detectors with $\phi_{MIN} < |\phi| < \phi_{MAX}$.

7. The method of claim 6 wherein using a first weighting scheme comprises:

identifying an unused portion of the complete set of fan beam projection data; and setting the unused portion of the complete set of fan beam projection data to zero.

8. The method of claim 7 wherein the unused portion of the complete set of fan beam data defines an unused portion of the plurality of projection angles of the complete set of fan beam projection data.

9. The method of claim 6 wherein using a second weighting scheme comprises:

identifying an unused portion of the complete set of fan beam projection data; and setting the unused portion of the complete set of fan beam projection data to zero.

10. The method of claim 9 wherein the unused portion of the complete set of fan beam projection data defines unused detectors in the array of detectors, the fan beam projection data acquired by the unused detectors being set to zero.

11. The method of claim 10 wherein the unused detectors are at detector angles $\phi$ such that $\phi_{MIN} < |\phi| \leq \phi_{MAX}$.

12. The method of claim 6 further comprising feathering the first and second weighting schemes for $|\phi| < \phi_{MIN}$.

13. The method of claim 12 wherein the feathering step comprises using linear feathering functions.

14. The method of claim 12 wherein the feathering step comprises using quadratic feathering functions.

15. The method of claim 12 wherein the feathering step is performed over an angle subtended by ten detectors.

16. The method of claim 1 further comprising converting the fan beam projection data to parallel projection data.

17. An apparatus for generating tomographic image data for an object, said apparatus comprising:

a radiation source for directing radiation through the object;

an array of detectors for receiving the radiation from the object to acquire fan beam projection data used to generate the image data for the object;

means for rotating the array of detectors and the radiation source about a center of rotation in the object through a plurality of projection angles to acquire the fan beam projection data, the ends of the array of detectors defining a fan angle having an apex defined by the radiation source, a line connecting the radiation source and the center of rotation dividing the fan angle into a first partial fan angle and a second partial fan angle, the first and second partial fan angles being unequal, wherein each line connecting each detector in the array of detectors and the radiation source defines a detector angle $\phi$ with the line connecting the radiation source and the center of rotation, the smaller of the first and second partial fan angles being $\phi_{MIN}$ and the larger of the first and second partial fan angles being $\phi_{MAX}$; and means for generating a slice of image data using a subset of a complete set of fan beam projection data for the slice, wherein the complete set of fan beam projection data for the slice comprises all of the fan beam projection data available from a complete revolution of the radiation source and the array of detectors about the center of rotation.

18. The apparatus of claim 17 wherein at least a portion of the object lies outside a field of view of the array of detectors.

19. The apparatus of claim 17 wherein the means for generating the slice of image data uses fan beam projection data acquired by a subset of the detectors in the array of detectors.

20. The apparatus of claim 17 wherein the means for generating the slice of image data uses fan beam projection data acquired at fewer than all of the fan beam projection angles for a complete revolution of the radiation source and the array of detectors about the center of rotation.

21. The apparatus of claim 17 further comprising means for weighting the fan beam projection data.

22. The apparatus of claim 21 wherein the means for weighting the fan beam projection data comprises:

means for applying a first weighting scheme to weight data acquired by detectors with $|\phi|<\phi_{MIN}$; and means for applying a second weighting scheme to weight data acquired by detectors with $\phi_{MIN}<|\phi|<\phi_{MAX}$.

23. The apparatus of claim 22 wherein the means for applying a first weighting scheme comprises:

means for identifying an unused portion of the complete set of fan beam projection data; and means for setting the unused portion of the complete set of fan beam projection data to zero.

24. The apparatus of claim 23 wherein the means for identifying an unused portion of the complete set of fan beam projection data defines an unused portion of the plurality of projection angles of the complete set of fan beam projection data.

25. The apparatus of claim 22 wherein the means for applying a second weighting scheme comprises:

means for identifying an unused portion of the complete set of fan beam projection data; and means for setting the unused portion of the complete set of fan beam projection data to zero.

26. The apparatus of claim 25 wherein the means for identifying an unused portion of the complete set of fan beam projection data defines unused detectors in the array of detectors, the fan beam projection data acquired by the unused detectors being set to zero.

27. The apparatus of claim 26 wherein the unused detectors are at detector angles $\phi$ such that $\phi_{MIN}<|\phi|<\phi_{MAX}$.

28. The apparatus of claim 22 further comprising means for feathering the first and second weighting schemes for $|\phi|<\phi_{MIN}$.

29. The apparatus of claim 28 wherein the means for feathering uses a linear feathering function.

30. The apparatus of claim 28 wherein the means for feathering uses a quadratic feathering function.

31. The apparatus for claim 28 wherein the means for feathering operates over an angle subtended by ten detectors.

32. The apparatus of claim 17 further comprising means for converting the fan beam projection data to parallel projection data.

* * * * *